US009382213B2

(12) United States Patent
Wright et al.

(10) Patent No.: US 9,382,213 B2
(45) Date of Patent: Jul. 5, 2016

(54) HETEROCYCLIC AND CYCLIC ANALOGS OF PROPARGYL-LINKED INHIBITORS OF DIHYDROFOLATE REDUCTASE

(71) Applicants: Dennis L Wright, Storrs, CT (US); Amy C Anderson, Storrs, CT (US); Grant Sormunen, Athens, OH (US)

(72) Inventors: Dennis L Wright, Storrs, CT (US); Amy C Anderson, Storrs, CT (US); Grant Sormunen, Athens, OH (US)

(73) Assignees: PROMILIAD BIOPHARMA INC., Alberton, MT (US); UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 14/620,997

(22) Filed: Feb. 12, 2015

(65) Prior Publication Data

US 2015/0225353 A1 Aug. 13, 2015

Related U.S. Application Data

(60) Provisional application No. 61/939,190, filed on Feb. 12, 2014.

(51) Int. Cl.
| | |
|---|---|
| *C07D 239/48* | (2006.01) |
| *A61K 31/505* | (2006.01) |
| *C07D 401/06* | (2006.01) |
| *C07D 403/06* | (2006.01) |
| *C07D 401/14* | (2006.01) |
| *C07D 409/14* | (2006.01) |
| *C07D 405/14* | (2006.01) |
| *C07D 239/42* | (2006.01) |

(52) U.S. Cl.
CPC ............ *C07D 239/48* (2013.01); *A61K 31/505* (2013.01); *C07D 239/42* (2013.01); *C07D 401/06* (2013.01); *C07D 401/14* (2013.01); *C07D 403/06* (2013.01); *C07D 405/14* (2013.01); *C07D 409/14* (2013.01)

(58) Field of Classification Search
CPC .. C07D 239/42; C07D 239/48; C07D 401/06; C07D 401/14; C07D 403/06; A61K 31/505
USPC ............................ 544/323, 324, 325; 514/275
See application file for complete search history.

(56) References Cited

U.S. PATENT DOCUMENTS

| | | | |
|---|---|---|---|
| 5,622,954 A | 4/1997 | Henrie, II et al. | |
| 8,426,432 B2 | 4/2013 | Anderson et al. | |
| 8,853,228 B2 | 10/2014 | Anderson et al. | |
| 2012/0196859 A1* | 8/2012 | Anderson | C07D 239/42 514/235.8 |

FOREIGN PATENT DOCUMENTS

| | | |
|---|---|---|
| WO | 98/20878 A1 | 5/1998 |
| WO | 2009/025919 A2 | 2/2009 |

OTHER PUBLICATIONS

N.E. Sharpless et al., Nature Reviews Drug Discovery 1-14, 2 (2006).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
G-Dayanandan et al., Propargyl linked antifolates are dual inhibitors of Candida albicans and Candida glabrata, Journal of Medicinal Chemistry, vol. 57, pp. 2643-2656 (Feb. 25, 2014).*
Anderson et al, Journal of Medicinal Chemistry (2007), 50(5):940-950.
Liu et al, Chem Biol Drug Des 2009; 73:62-74.
Beierlein et al, Journal of Medicinal Chemistry, 53(20):7327-7336 (Oct. 28, 2010).
Liu et al, Eukaryotic Cell, 8(4):483-486 (Apr. 2009).
Bolstad et al, Journal of Medicinal Chemistry, 51(21):6839-6852 (Nov. 13, 2008).
Pelphrey et al, Journal of Medicinal Chemistry, 50:940-950 (2007).
Patani, Chemical Reviews, 96(8):3147-3176 (1996).
Popov, Proteins: Structure, Function and Bioinformatics, 66:375-387 (2007).
Wright et al, "Antifolate agents: a patent review (2006)-(2010)", Expert Opinion, Jan. 16, 2011, 1-11.

* cited by examiner

*Primary Examiner* — Deepak Rao
(74) *Attorney, Agent, or Firm* — Porter Wright Morris & Arthur LLP

(57) ABSTRACT

Compounds of Formula I and Formula IA are inhibitors of dihydrofolate reductase and are suitable for use in compositions and methods for dihydrofolate reductase inhibition or, more specifically, treatment of a fungal infection, a bacterial infection or a protozoal infection, and, in specific embodiments, treatment of a fungal infection caused by *C. albicans* or *C. glabrata*:

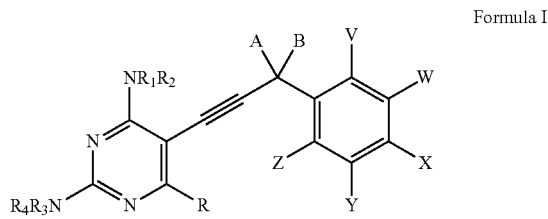

Formula I

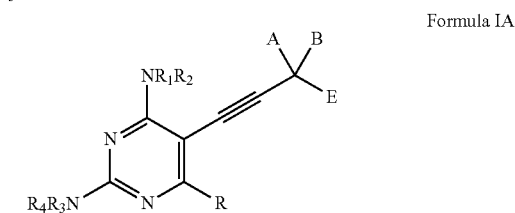

Formula IA wherein R, $R_1$, $R_2$, $R_3$, $R_4$, A, B, E, V, W, X, Y and Z are as defined herein.

24 Claims, No Drawings

HETEROCYCLIC AND CYCLIC ANALOGS OF PROPARGYL-LINKED INHIBITORS OF DIHYDROFOLATE REDUCTASE

RELATED APPLICATION

This application claims priority under 35 U.S.C. 119 of U.S. Application Ser. No. 61/939,190 filed Feb. 12, 2014, and U.S. Application Ser. No. 61/939,190 filed Feb. 12, 2014 is incorporated herein in its entirety by reference.

STATEMENT REGARDING FEDERALLY SPONSORED RESEARCH

This invention was made with government support under Grant No. GM067542 awarded by the National Institutes of Health. The government has certain rights in the invention.

TECHNICAL FIELD

The present invention is directed to heterocyclic and cyclic analogs of 2,4-diaminopyrimidine propargyl-linked compounds which are highly potent inhibitors of dihydrofolate reductase and, more specifically, antifungal agents targeting *Candida* species, including *Candida albicans* and *Candida glabrata*. These analogs also exhibit minimal mammalian cell cytotoxicity. In selected embodiments, the compounds contain multiple cyclic substitutions and in selected embodiments, the compounds contain multiple heterocyclic substitutions. The invention is also directed to treatment methods employing such compounds.

BACKGROUND OF THE INVENTION

Although bloodstream infections (BSI) are frequently attributed to bacterial pathogens, fungal infections caused by *Candida* species actually represent the fourth leading cause of BSI in the United States and present a specific risk for immune compromised patients (Morrell et al, Delaying the Empiric Treatment of *Candida* Bloodstream Infections until Positive Blood Culture Results Are Obtained: a Potential Risk Factor for Hospital Mortality, *Antimicrob. Agents Chemother.*, 49:3640-3645 (2005); Pfaller et al, Epidemiology of Invasive Mycoses in North America, *Crit. Rev. Microbiol.*, 36:1-53 (2010); Falagas et al, Relative frequency of *albicans* and the various nonalbicans *Candida* spp among candidemia isolates from inpatients in various parts of the world: a systematic review, *Int. J. Infect. Dis.*, 14:e954-e966 (2010)). The incidence of candidiasis has increased dramatically over the previous two decades, resulting in significant morbidity, mortality (40-49%6) and increased healthcare costs. Among the *Candida* spp., *C. albicans* is the primary cause of BSI (45.6%), followed by *C. glabrata* (26.0%) (Horn et al, Clinical characteristics of 2,019 patients with candidemia: data from the PATH Alliance Registry, *Clin. Infect. Dis.*, 48:1695-1703 (2009)). However, *C. glabrata* represents an increasing threat as studies show that while *C. glabrata* accounted for 18% of BSI candidemia between 1992-2001, that fraction rose to 26% in the time period 2001-2007.

The administration of effective empirical therapy for fungal BSI significantly reduces mortality (27% vs 46%) (Parkins et al, Adequacy of empirical antifungal therapy and effect on outcome among patients with invasive *Candida* species infection, *J. Antimicrob. Chemother.*, 60:613-6186 (2007)). Unfortunately, however, there is often a significant delay in the correct diagnosis of candidiasis, identification of the species and start of therapy to which the strain is sensitive. While *C. albicans* remains relatively sensitive to azoles, flucytosine and echinocandins, *C. glabrata* exhibits decreased sensitivity for fluconazole, with evidence of cross-resistance to other azoles such as voriconazole (Borst et al, Rapid Acquisition of Stable Azole Resistance by *Candida glabrata* Isolates Obtained before the Clinical Introduction of Fluconazole, *Antimicrob. Agents Chemother.*, 49:783-787 (2005); Magill et al, Triazole cross-resistance among *Candida* spp.: case report, occurrence among bloodstream isolates, and implications for antifungal therapy, *J. Clin. Microbiol.*, 44:529-535 (2006)); 11% of fluconazole-resistant strains are reportedly now also resistant to echinocandins (Pfaller et al, Decreased Susceptibility and Resistance to Echinocandins among Fluconazole-Resistant Bloodstream Isolates of *Candida glabrata*, *J. Clin. Microbiol.*, 50:1199-1203 (2012)). The increased incidence of *C. glabrata* as a causative agent of candidiasis along with the increasing drug resistance in this strain makes new antifungals that target *C. glabrata* a clear priority. However, an ideal agent would target both *C. albicans* and *C. glabrata* as *C. albicans* infections continue to be a major health risk and the two are difficult to distinguish in a clinical setting.

Targeting the essential enzyme dihydrofolate reductase (DHFR) has proven to be an effective strategy for both prokaryotic (eg. trimethoprim) and protozoal (eg. pyrimethamine) pathogens, but is not widely used clinically in the treatment of invasive fungal infections. DHFR plays a critical role in the turnover of folate cofactors; effective inhibition of DHFR produces a blockade in thymidine synthesis leading to "thymineless" death. As humans are also dependent on active DHFR, it is important that there is selective inhibition of the pathogenic enzyme. Fortunately, there are several important active site differences between human and *Candida* species that can be exploited for selectivity. It is widely recognized that the development of antimetabolites targeting *C. albicans* can be complicated by pronounced inconsistencies between target inhibition and antifungal activity. Attempts to study whether the cell wall or membrane permeability affects the uptake of six unrelated antibiotics targeting intracellular proteins failed to derive a direct relationship (Ziegelbauer, A dual labelling method for measuring uptake of low molecular weight compounds into the pathogenic yeast *Candida albicans*, *Med. Mycol.*, 36:323-330 (1998)). These same inconsistencies have also complicated the development of antifungal antifolates. For example, Kuyper et al hypothesized that molecular weight was inversely related to antifungal activity and pursued the synthesis and evaluation of over 150 low molecular weight analogs; although the effort produced potent, albeit nonselective inhibitors with good antifungal activity, lead optimization of the antifolates against *C. albicans* was hindered by lack of correlation between enzyme inhibition and antifungal activity, and the researchers concluded that there was no relationship between activity and inhibitor size or lipophilicity but that differences in transport phenomenon could still play an important role in antifungal activity (High-affinity inhibitors of dihydrofolate reductase: antimicrobial and anticancer activities of 7,8-dialkyl-1,3-diaminopyrrolo[3,2-f]quinazolines with small molecular size, *J. Med. Chem.*, 39:892-903 (1996)). More recently, Otzen et al reported a group of potent *C. albicans* DHFR inhibitors based on a benzyl(oxy)pyrimidine scaffold (Folate-synthesizing enzyme system as target for development of inhibitors and inhibitors combinations against *Candida albicans*—Synthesis and biological activity of new 2,4-diaminopyrimidines and 4'-substituted 4-aminodiphenyl sulfones, *J. Med. Chem.*, 47:240-253 (2004)). However, these compounds did not exhibit in vitro antifungal activity. After showing that the compounds were not generally susceptible to efflux, the authors of this study also speculated that the compounds were unable to enter *C. albicans*.

The present inventors previously discovered new DHFR inhibitors comprising a 2,4-diaminopyrimidine ring with a propargyl linker to an optionally substituted aryl or heteroaryl ring, as disclosed in U.S. Pat. Nos. 8,426,432 B2 and 8,853,228 B2, each of which is incorporated herein in its entirety. The compounds are pyrimidine derivatives that function as DHFR inhibitors. However, additional DHFR inhibitors and, more specifically, antifungal agents targeting *Candida albicans* and *Candida glabrata*, are desired.

SUMMARY OF THE INVENTION

It is therefore an object of the invention to provide new DHFR inhibitors and, in a more specific embodiment, DHFR inhibitors comprising antifungal agents. In further embodiments, it is an object of the invention to provide antifungal agents targeting *Candida albicans* and *Candida glabrata*. In yet further embodiments, it is an object to provide compositions and methods of treatment employing such DHFR inhibitors.

In one embodiment, the invention is directed to compounds of Formula I, and to compositions and methods employing such compounds:

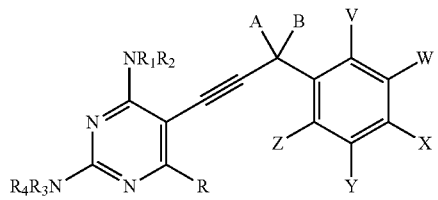

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, alkoxyalkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkylcarbonyl, haloalkylcarbonyl, and cyanoalkylcarbonyl;

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl;

wherein at least one of V, W, X, Y, and Z is an alkoxy group;

wherein at least one of V, W, X, Y, and Z is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

In another embodiment, the invention is directed to compounds of Formula IA, and to compositions and methods employing such compounds:

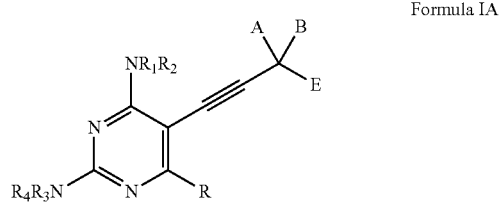

Formula IA wherein R, $R_1$, $R_2$, $R_3$, $R_4$, and A and B are defined as above as substituents in Formula I; and wherein E is a heterocyclic substituent E1 wherein at least one heteroatom is N, S or O, and wherein the heterocyclic substituent E1 itself is substituted with a heterocyclic or aryl substituent E2, which, in turn, may optionally be substituted one or more times with $C_1$ to $C_5$ alkyl, halogen, hydroxy, lower haloalkyl, lower alkoxy, lower haloalkoxy, or lower alkoxyalkyl, and the heterocyclic substituent E1 is optionally substituted one or more times with $C_1$ to $C_5$ alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, or dialkylsilyloxy;

wherein each "lower" used in conjunction with any of the above groups is individually $C_1$ to $C_6$, or a pharmaceutically acceptable salt thereof.

In further embodiments, the invention is directed to a method of inhibiting dihydrofolate reductase comprising administering a pharmaceutically effective amount of a compound according to the invention to an individual in need thereof. In specific embodiments, the reductase is a mammalian enzyme.

In further embodiments, the invention is directed to a method of treating an individual that has a fungal infection, a bacterial infection, or a protozoal infection comprising administering a pharmaceutically effective amount of a compound according to the invention to the individual. In additional embodiments, the invention is directed to a method of treating cancer in an individual comprising administering a pharmaceutically effective amount of a compound according to the invention to the individual.

The compounds, compositions and methods of the invention are advantageous in providing new therapies for DHFR inhibition. Additional objects and advantages will be more apparent in view of the detailed description.

DETAILED DESCRIPTION

The compounds of the invention are 2,4-diaminopyrimidine ring compounds with a propargyl linker to a specified heterocyclic or cyclic moiety. The inhibition of DHFR and, in a specific embodiment, the growth of *C. albicans*, is dependent on the shape of the inhibitor and extended compounds, and, in some embodiments, extended para-linked compounds, are more effective than compact compounds or compact meta-linked compounds. Using crystal structures of DHFR from *C. albicans* and *C. glabrata* bound to lead compounds, the present compounds are designed to inhibit both species. Both the shape and distribution of polar functionality contribute to achieving dual antifungal activity.

In one embodiment, the compound is of Formula I:

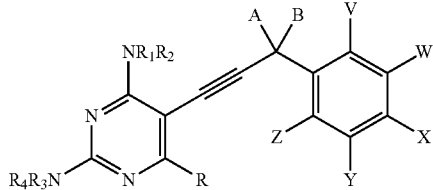

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl (e.g., cyclohexyl), alkoxyalkyl (e.g., —$C_3H_6OC_2H_5$), alkoxyalkoxyalkyl (e.g., —$C_2H_4OC_2H_4OC_2H_5$), arylalkyl (e.g., phenylmethyl or 2-pyridylmethyl), alkylcarbonyl (e.g., —(C=O)$CH_3$, —(C=O)CH($CH_3$)$_2$, —(C=O)$C_{11}H_{23}$), cycloalkylcarbonyl (e.g., cyclohexylcarbonyl), alkoxycarbonyl (e.g., —(C=O)O$C_2H_5$), alkoxyalkylcarbonyl (e.g., —(C=O)$C_2H_4OC_2H_5$), alkoxyalkoxyalkylcarbonyl (e.g., —(C=O)$C_2H_4OC_2H_4OC_2H_5$), arylcarbonyl (e.g., benzoyl), pyridinylcarbonyl (e.g., 3-pyridinylcarbonyl), aryloxyalkylcarbonyl (e.g., —C(=O)$CH_2OC_6H_5$), haloalkylcarbonyl (e.g., —C(=O)(CH$_2$)$_2$F), and cyanoalkylcarbonyl (e.g., —C(=O)(CH$_2$)$_3$CN);

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl;

wherein at least one of V, W, X, Y, and Z is an alkoxy group;

wherein at least one of V, W, X, Y, and Z is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

In one embodiment of the compound of Formula I, at least one of V, W, X, Y, and Z is an alkoxy group or, more specifically, a methoxy group. In another embodiment, V is an alkoxy group or, more specifically, a methoxy group. In specific embodiments, X is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine. In more specific embodiments, X is a phenyl group having at least one substituent selected from the group consisting of hydroxyl, cyano, carbamate (—OC(O)NH$_2$), methoxycarbonyl, methylamine and dimethylamine. In additional embodiments, the remainder of W, Y, and Z are each independently selected from the group consisting of hydrogen, $C_{1-5}$alkyl, halogen, hydroxy, lower haloalkyl, and lower alkoxy. In a more specific embodiment, W, Y, and Z are each hydrogen.

In another embodiment, the compound is of Formula IA:

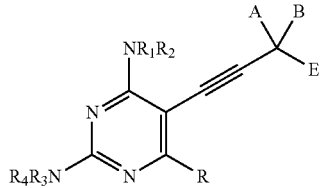

Formula IA wherein R, $R_1$, $R_2$, $R_3$, $R_4$, and A and B are defined as above as substituents in Formula I; and wherein E is a heterocyclic substituent E1 wherein at least one heteroatom is N, S or O, and wherein the heterocyclic substituent E1 itself is substituted with a heterocyclic or aryl substituent E2, which, in turn, may optionally be substituted one or more times with $C_1$ to $C_5$ alkyl, halogen, hydroxy, lower haloalkyl, lower alkoxy, lower haloalkoxy, or lower alkoxyalkyl, and the heterocyclic substituent E1 is optionally substituted one or more times with $C_1$ to $C_5$ alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, or dialkylsilyloxy;

wherein each "lower" used in conjunction with any of the above groups is individually $C_1$ to $C_6$, or a pharmaceutically acceptable salt thereof.

In specific embodiments of the compound of Formula IA, the heterocyclic substituent E1 is a 5- to 8-membered, saturated or unsaturated mono- or bicyclic-ring, and the substituent E2 is a 5- to 8-membered, saturated or unsaturated monoor bicyclic-ring or phenyl, optionally containing a heteroatom in the ring. In additional embodiments, the heterocyclic substituents E1 and E2 are individually selected from the group consisting of piperidine, perhydropyrimidine, morpholine, pyridine, pyrimidine, indole, isoindole, quinoline, isoquinoline, oxazole, thiazole, imidazole, furan, thiophene, pyrrole, pyrazole, triazole, tetrazole, isoxazole, oxadiazole, thiadiazole, isothiazole, pyridazine, pyrazine, benzofuran, benzothiophene, benzodioxole, indazole, piperazine, pyrrolidine, dioxolane, tetrahydrofuran, and tetrahydropyran, and may be optionally substituted one or more times with $C_1$ to $C_5$ alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, or dialkylsilyloxy. The E2 group may be attached to the E1 group in a meta or para arrangement.

In additional specific embodiments of the compound of Formula IA, E1 is selected from the group consisting of pyridine, pyrimidine, pyrazole, or triazole, optionally substituted one or more times with $C_1$ to $C_5$ alkyl, halogen, hydroxy, lower haloalkyl, lower alkoxy, lower haloalkoxy, or lower alkoxyalkyl, and E2 is attached to the E1 group in a meta or para arrangement and is phenyl or phenyl with one to three substituents individually selected from the group consisting of $C_1$ to $C_5$ alkyl, halogen, lower haloalkyl, lower alkoxy, lower haloalkoxy, lower alkoxyalkyl, and lower alkoxycarbonyl.

In selected embodiments of the compounds of Formula I and Formula IA, R is hydrogen or $C_{1-5}$alkyl, $R_1$, $R_2$, $R_3$, and $R_4$ are each independently selected from the group consisting of hydrogen, $C_{1-5}$alkyl, cycloalkyl, and alkoxyalkyl, and A and B are each independently hydrogen or $C_{1-5}$alkyl. In further embodiments, one of A and B is hydrogen and the other is $C_{1-5}$alkyl.

The compounds of Formula I may be prepared by various methods. In one embodiment, Reaction Scheme 1 is employed, wherein a central 4-bromo-acetophenone moiety such as compound 7, 8 is subjected in step (a) to Suzuki cross-coupling with an aryl boronic acid to give a biaryl derivative 9-17 with a key acetyl group that can be taken on to the propargylated intermediate 18-27 through steps (b)-(d). Final cross-coupling with 6-ethyl-5-iodo-2,4-diaminopyrimidine yields the inhibitors of Formula I:

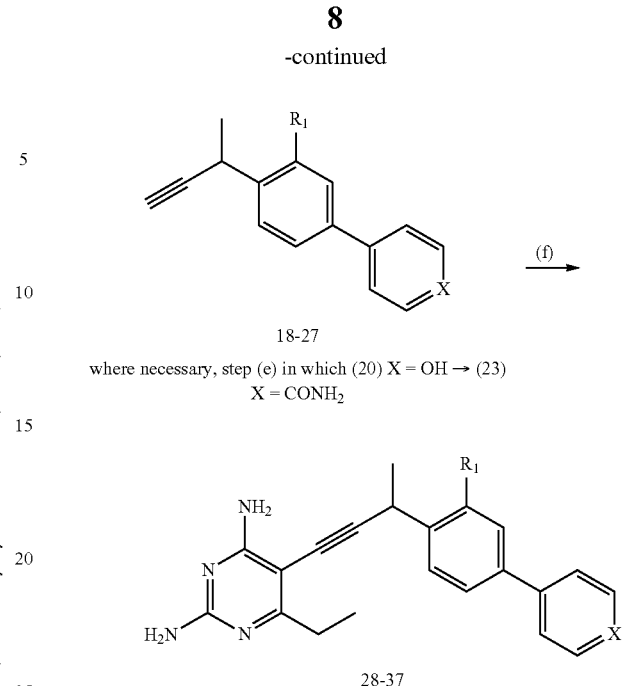

where necessary, step (e) in which (20) X = OH → (23) X = CONH$_2$

Reaction Scheme 1: (a) aryl-boronic acid, Pd(PPh$_3$)$_2$Cl$_2$, Cs$_2$CO$_3$, dioxane, 80° C.; (b) Ph$_3$P=CHOMe, THF; (c) Hg(OAc)$_2$, KI, THF/H$_2$O; (d) dimethyl(1-diazo-2-oxopropyl)phosphonate, K$_2$CO$_3$, MeOH; (e) ClSO$_2$NCO, CH$_2$Cl$_2$; (f) 6-ethyl, 5-iodo-2,4-diaminopyrimidine, Pd(PPh$_3$)$_2$Cl$_2$, Et$_3$N, DMF.

Exemplary compounds prepared using Reaction Scheme 1 as described in the Examples include the following compounds 30 and 32-35:

30: $R_1$=OCH3, X=C—OH
32: $R_1$=OCH3, X=C—CN
33: $R_1$=OCH3, X=C—OC(=O)NH$_2$
34: $R_1$=OCH3, X=C—C(=O)OCH$_3$
35: $R_1$=OCH3, X=C—NMe$_2$.

The compounds of Formula IA may be prepared by various methods. In one embodiment, Reaction Scheme 2 is employed:

Reaction Scheme 1

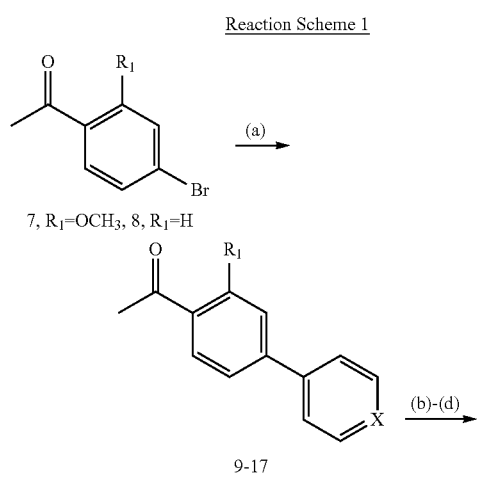

Reaction Scheme 2

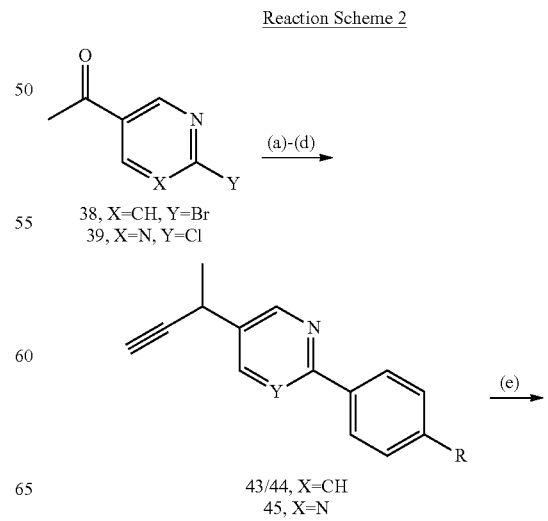

-continued

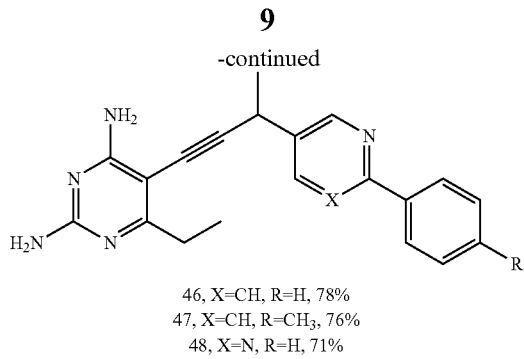

46, X=CH, R=H, 78%
47, X=CH, R=CH₃, 76%
48, X=N, R=H, 71%

Reaction Scheme 2: (a) aryl-boronic acid, Pd(PPh₃)₂Cl₂, Na₂CO₃, CH₃CN, H₂O 80° C.; (b) Ph₃P═CHOMe, THF; (c) Hg(OAc)₂, KI, THF/H₂O; (d) dimethyl(1-diazo-2-oxopropyl)phosphonate, K₂CO₃, MeOH; (e) 6-ethyl, 5-iodo-2,4-diaminopyrimidine, Pd(PPh₃)₂Cl₂, CuI, Et₃N, DMF.

Exemplary compounds prepared using Reaction Scheme 2 as described in the Examples include the indicated compounds 46-48.

Additional exemplary compounds of Formula IA include the following:

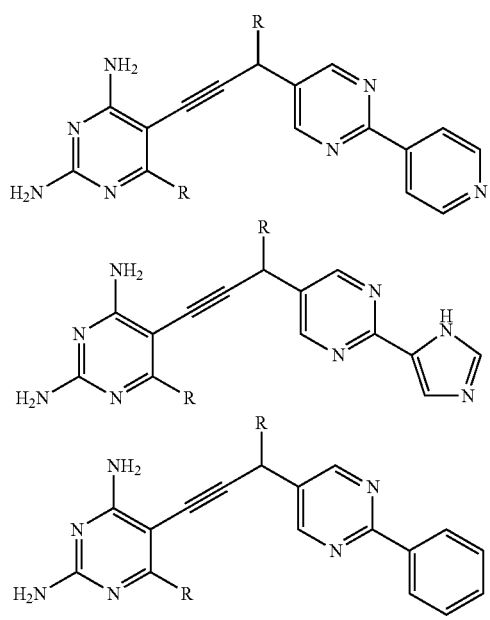

wherein each R is independently hydrogen or $C_{1-5}$ alkyl.

Pharmaceutical Compositions

In further embodiments, the invention is directed to pharmaceutical compositions comprising a compound of Formula I or Formula IA in combination with one or more pharmaceutically acceptable diluents, excipients or carriers. One or more of the compounds can be prepared in a physiologically acceptable formulation, such as in a pharmaceutically acceptable carrier, using known techniques. For example, the compound is combined with a pharmaceutically acceptable excipient to form a therapeutic composition.

In another embodiment, the compositions provided herein can be administered together with, or in addition to, sulfa compounds to form therapeutic pharmaceutical compositions. It is recognized in the art that sulfa compounds exhibit high activity against pathogenic bacteria. Non-limiting examples of sulfa compounds and the processes by which the sulfa compounds are made is provided in U.S. Pat. No. 3,091,610, which is herein incorporated by reference in its entirety for all purposes.

The compositions provided herein may be administered in the form of a solid, liquid or aerosol. Examples of solid compositions include pills, creams, and implantable dosage units. Pills may be administered orally. Therapeutic creams may be administered topically. Implantable dosage units may be administered locally, or may be implanted for systematic release of the therapeutic composition, for example, subcutaneously. Examples of liquid compositions include formulations adapted for injection intramuscularly, subcutaneously, intravenously, or intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal or parenteral (for example, intravenous, subcutaneous, or intramuscular) routes. In addition, the composition may be incorporated into a delayed release, controlled release and/or sustained release formulation. The method includes administration of a single dose, administration of repeated doses at predetermined time intervals, and sustained administration for a predetermined period of time.

A sustained release matrix, as used herein, includes a matrix made of materials, usually biodegradable polymer(s), that are degradable by enzymatic or acid/base hydrolysis or by dissolution. The sustained release matrix polymers are implanted in the vicinity of where delivery is desired. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It should be understood that in addition to the ingredients particularly mentioned above, the formulations of the present invention may include other agents conventional in the art having regard to the type of formulation in question.

The dosage of the composition will depend on the progression of infection or cancer, the particular composition used, and other clinical factors such as weight and condition of the patient, and the route of administration.

Methods

In further embodiments, the invention is directed to a method of inhibiting dihydrofolate reductase comprising administering a pharmaceutically effective amount of a compound of Formula I or Formula IA to an individual in need thereof. In selected embodiments, the reductase is a mammalian enzyme.

In further embodiments, the invention is directed to a method of treating an individual that has a fungal infection comprising administering a pharmaceutically effective amount of a compound of Formula I or Formula IA to the individual. In a more specific embodiment, the fungal infection is caused by *Candida* species, and, in a more specific embodiment, the fungal infection is caused by *C. albicans* or *C. glabrata*.

In further embodiments, the invention is directed to a method of treating a bacterial infection or a protozoal infection comprising administering a pharmaceutically effective amount of a compound of Formula I or Formula IA to the individual. In additional embodiments, the invention is directed to a method of treating cancer in an individual and the compound of Formula I or Formula IA is administered to the individual in a dose sufficient to treat cancer.

Treatment of a patient having a fungal, bacterial or protozoal disease or cancer can be accomplished by administering to the patient a pharmaceutically acceptable composition containing one of more of the compounds described, as described herein, at an effective dosage. Effective results may be obtained with a single dose. Multiple doses may be necessary to achieve optimal and sustained benefits. The compounds can be provided as substantially purified compositions or placed in pharmaceutically acceptable formulations. The formulations may be administered for immediate, controlled or sustained release using formulations and methods known to those of ordinary skill in the art as described above. These formulations can be administered by standard routes. In general, the compositions may be administered by various routes (e.g., intravenous, transdermal, intraperitoneal, intraspinal, subcutaneous or intramuscular) as described above.

The effective dosage of one or more of the pharmaceutical compositions provided herein will depend on the disease state or condition being treated and other clinical factors such as weight and condition of the animal or human and the route of administration. Depending upon the half-life of the compound in the particular animal or human, it can be administered between several times per day to once a month or less. The methods described herein contemplate single as well as multiple administrations, given either simultaneously or over an extended period of time.

It is to be understood that the methods provided herein have applications for both human, mammalian and veterinary use. It is also to be understood that the term "individual" as used herein refers to an animal, human, mammal or other patient in need of treatment using the compounds described herein.

The following examples are provide for illustration only and are non-limiting of the invention.

EXAMPLES

The following general procedures were employed throughout the examples unless otherwise indicated.

The $^1H$ and $^{13}C$ NMR spectra were recorded on Bruker instruments at 500 MHz. Chemical shifts are reported in ppm and are referenced to residual $CHCl_3$ solvent; 7.24 and 77.23 ppm for $^1H$ and $^{13}C$, residual solvent MeOH; 4.78, 3.31 and 49.15 ppm respectively. Melting points were recorded on Mel-Temp 3.0 apparatus and are uncorrected. The high-resolution mass spectrometry was provided by the Notre Dame Mass Spectrometry Laboratory and University of Connecticut Mass Spectrometry Laboratory using AccuTOF mass spectrometer and/or using DART source. IR data were obtained using Alpha diamond ATR probe. TLC analyses were performed on Sorbent Technologies silica gel HL TLC plates. All glassware was oven-dried and allowed to cool under an argon atmosphere. Anhydrous dichloromethane, ether, and tetrahydrofuran were used directly from Baker Cycle-Tainers. Anhydrous dimethylformamide was purchased from Acros and degassed by purging with argon. Anhydrous triethylamine was purchased from Aldrich and degassed by purging with argon. All reagents were used directly from commercial sources unless otherwise stated. Boronic acids for Suzuki coupling were purchased from Frontier Scientific, Inc. 4' bromoacetophenone and 5-acetyl-2-bromopyridine were purchased from Sigma Aldrich. The starting bromo ketones 7, 40, Ohira-Bestmann reagent, 2,4-diamino-6-ethyl-5-iodopyrimidine were synthesized according to literature procedures.

Example 1

Preparation of Compound 30

Compound 30, 4'4-[3-(2,4-Diamino-6-ethyl-pyrimidin-5-yl)-1-methyl-prop-2-ynyl]-3'-methoxy-biphenyl-4-ol, of Reaction Scheme 1 was prepared as described.

1-[3-Methoxy-4'-(tetrahydro-pyran-2-yloxy)-biphenyl-4-yl]-ethanone (11)

According to the general Suzuki coupling procedure, ketone 7 (0.49 g, 2.17 mmol), 4-(tetrahydro-2H-pyran-2-yloxy)phenylboronic acid (0.96 g, 4.34 mmol), $Cs_2CO_3$ (2.12 g, 6.51 mmol), $Pd(PPh_3)_2Cl_2$ (0.15 g, 0.22 mmol, 10% Pd) and anhydrous dioxane (6 mL) were heated at 80° C. for 14 h (overnight). Following the general workup and flash chromatography ($SiO_2$, 20 g, 10% EtOAc/hexanes) biaryl ketone 11 was obtained as a pale white solid (0.430 g, 61%): TLC $R_f$=0.5 (25% EtOAc/hexanes); mp 86.7-89.7° C.; $^1H$ NMR (500 MHz, $CDCl_3$) δ 7.80 (d, J=8.0 Hz, 1H), 7.52 (d, J=7.9 Hz, 2H), 7.30-6.97 (m, 4H), 5.46 (s, 1H), 3.95 (s, 3H), 3.92-3.87 (m, 1H), 3.62-3.59 (m, 1H) 2.62 (s, 3H), 2.05-1.97 (m, 1H), 1.87-1.86 (m, 2H), 1.72-1.65 (m, 2H), 1.60-1.58 (m, 1H); $^{13}C$ NMR (125 MHz, $CDCl_3$) δ 199.2, 159.5, 157.5, 146.7, 133.5, 131.2, 128.4, 126.3, 119.1, 116.9, 110.0, 96.4, 62.1, 55.6, 32.0, 30.4, 25.3, 18.8; IR (neat $cm^{-1}$) 2940, 2872, 2847, 1656, 1598, 1358, 1280, 1177, 1019, 813, 518; HRMS (DART, $M_++H$) m/z 327.1612 (calculated for $C_{20}H_{23}O_4$, 327.1596).

3'-Methoxy-4'-(1-methyl-prop-2-ynyl)-biphenyl-4-ol (20)

According to a general procedure for homologation, methoxymethyl triphenylphosphonium chloride (4.71 g, 13.73 mmol) in dry THF (37 mL), $NaO_tBu$ (1.58 g, 16.5 mmol), ketone 11 (1.79 g, 5.49 mmol) in THF (7 mL) were stirred at 0° C. Following the general workup, the mixture of enol ethers (1.77 g, 5.00 mmol) in $THF/H_2O$ (9:1, 17 mL) were hydrolyzed using $Hg(OAc)_2$ (4.8 g, 14.97 mmol) at room temperature. After the general extraction procedure, aldehyde (1.564 g, 4.65 mmol) in MeOH (20 mL), Ohira-Bestmann reagent (1.60 g, 8.4 mmol) dissolved (11 mL) in MeOH, powdered $K_2CO_3$ (1.337 g, 9.7 mmol) were stirred at 0° C. Following the general workup and flash chromatography ($SiO_2$, 30 g, 15% EtOAc/hexanes), O-THP alkyne was obtained as a pale white solid (0.84 g). Deprotection of O-THP alkyne was carried out by dissolving the protected alkyne (0.84 g, 2.5 mmol) in MeOH (150 mL) and cooled to 0° C. p-Toluenesulfonic acid (0.951 g, 2.5 mmol) was added and reaction allowed to warm to room temperature. The reaction was followed by TLC, diluted with water, neutralized with sat $NaHCO_3$ and extracted with ether. The organic extracts were washed with brine, dried over $MgSO_4$ and filtered. The filtrate was concentrated and purified by flash column chromatography ($SiO_2$, 30 g, 15% EtOAc/hexanes)

to give the terminal acetylene 20 as a white solid (0.61 g, 43% yield over 4 steps); TLC $R_f$=0.3 (25% EtOAc/hexanes); mp 90.2-91° C.; $^1$H NMR (500 MHz, CDCl$_3$) δ 7.57 (d, J=7.9 Hz, 1H), 7.45 (d, J=8.6 Hz, 2H), 7.11 (dd, J=7.9, 1.7 Hz, 1H), 6.98 (d, J=1.6 Hz, 1H), 6.88 (d, J=8.6 Hz, 2H), 4.18 (qd, J=7.0, 2.4 Hz, 1H), 3.88 (s, 3H), 2.20 (d, J=2.5 Hz, 1H), 1.45 (d, J=7.0 Hz, 3H); $^{13}$C NMR (125 MHz, CDCl$_3$) δ 156.5, 155.3, 141.0, 134.3, 129.7, 128.6, 128.2, 119.4, 115.8, 109.3, 87.8, 69.5, 55.7, 25.3, 22.9; IR (neat cm$^{-1}$) 3334. 3300, 2938, 1606, 1494, 1218, 807, 633; HRMS (DART, M$_+$+H) m/z 253.1224 (calculated for C$_{17}$H$_{17}$O$_2$, 253.1229).

4'-[3-(2,4-Diamino-6-ethyl-pyrimidin-5-yl)-1-methyl-prop-2-ynyl]-3'-methoxy-biphenyl-4-ol (30)

According to the general Sonogahisra coupling procedure, ethyl-iodopyrimidine (0.036 g, 0.14 mmol), CuI (0.0075 g, 0.039 mmol, 21 mol %), Pd(PPh$_3$)$_2$Cl$_2$ (0.009 g, 0.014 mmol, 10 mol %) and alkyne 20 (0.037 g, 0.15 mmol) were reacted in DMF/Et$_3$N (0.5 mL each) at 60° C. for 14 h. After the mixture was cooled, dark reddish brown solution was concentrated and the product was purified by flash chromatography (SiO$_2$, 5 g, 3% MeOH/CH$_2$Cl$_2$) to afford coupled pyrimidine 30 as a pale white powder (0.043 g, 79%) followed by reverse phase flash chromatography (NH$_2$ capped SiO$_2$, 3 g, 100% CH$_2$Cl$_2$, 1% MeOH/CH$_2$Cl$_2$) for biological evaluation: TLC $R_f$=0.06 (5% MeOH/CH$_2$Cl$_2$); mp 188.1-189.3° C.; $^1$H NMR (500 MHz, CDCl$_3$) δ 7.52 (d, J=7.8 Hz, 1H), 7.42 (d, J=8.6 Hz, 2H), 7.11 (dd, J=7.9, 1.7 Hz, 1H), 7.01 (d, J=1.7 Hz, 1H), 6.90 (d, J=8.6 Hz, 2H), 5.31 (s, 2H), 4.99 (s, 2H), 4.40 (q, J=7.0 Hz, 1H), 3.89 (s, 3H), 2.72 (q, J=7.6 Hz, 2H), 1.53 (d, J=7.0 Hz, 3H), 1.24 (t, J=7.6 Hz, 3H); $^{13}$C NMR (125 MHz, CDCl$_3$) δ 173.2, 164.4, 160.3, 156.5, 156.5, 141.4, 133.2, 129.9, 128.6, 128.0, 119.4, 116.1, 109.4, 102.9, 91.4, 73.9, 55.7, 29.7, 26.9, 22.9, 12.9; IR (neat cm$^{-1}$) 3470, 3371, 3337, 3173, 2970, 2930, 2871, 2341, 1726, 1547, 1438, 1217, 1028, 813; HRMS (ESI, M$_+$+H) m/z 389.1963 (calculated for C$_{23}$H$_{25}$N$_4$O$_2$, 389.1972); HPLC (a) $t_R$=6.8 mins, 99%, (b) $t_R$=8.23 mins, 99%.

Example 2

Preparation of Compound 32

Compound 32, 4'-[3-(2,4-Diamino-6-ethyl-pyrimidin-5-yl)-1-methyl-prop-2-ynyl]-3'-methoxy-biphenyl-4-carbonitrile, of Reaction Scheme 1 was prepared as described.

4'-Acetyl-3'-methoxy-biphenyl-4-carbonitrile (13)

According to the general Suzuki coupling procedure, ketone 7 (0.500 g, 2.18 mmol), 4-cyanophenylboronic acid (0.640 g, 4.36 mmol), Cs$_2$CO$_3$ (2.14 g, 6.55 mmol), Pd(PPh$_3$)$_2$Cl$_2$ (0.154 g, 0.22 mmol, 10% Pd) and anhydrous dioxane (6 mL) were heated at 80° C. for 14 h (overnight). Following the general workup and flash chromatography (SiO$_2$, 20 g, 10% EtOAc/hexanes) biaryl ketone 13 was obtained as a white solid (0.470 g, 86%): TLC $R_f$=0.4 (25% EtOAc/hexanes); mp 125-127.2° C.; $^1$H NMR (500 MHz, CDCl$_3$) δ 7.84 (d, J=8.0 Hz, 1H), 7.76-7.73 (m, 2H), 7.71-7.68 (m, 2H), 7.20 (dd, J=8.0, 1.6 Hz, 1H), 7.13 (d, J=1.5 Hz, 1H), 4.00 (s, 3H), 2.64 (s, 3H); $^{13}$C NMR (125 MHz, CDCl$_3$) δ 199.2, 159.5, 144.8, 144.7, 132.9, 131.5, 128.2, 128.1, 119.8, 118.8, 112.1, 110.7, 55.9, 32.0; IR (neat cm$^{-1}$) 3073, 3046, 2923, 2225, 1652, 1601, 1468, 1225, 1023, 812, 543; HRMS (DART, M$_+$+H) m/z 252.1032 (calculated for C$_{16}$H$_{14}$NO$_2$, 252.1024).

3'-Methoxy-4'-(1-methyl-prop-2-ynyl)-biphenyl-4-carbonitrile (22)

According to the general procedure for homologation, methoxymethyl triphenylphosphonium chloride (1.09 g, 3.18 mmol) in dry THF (4 mL), NaO$_t$Bu (0.382 g, 3.9 mmol), ketone 13 (0.400 g, 1.59 mmol) in THF (3 mL) were stirred at 0° C. Following the general workup, the mixture of enol ethers (0.330 g, 1.18 mmol) in THF/H$_2$O (9:1, 5 mL) were hydrolyzed using Hg(OAc)$_2$ (1.13 g, 3.5 mmol) at room temperature. After the general extraction procedure, aldehyde (0.285 g, 1.1 mmol) in MeOH (3 mL), Ohira-Bestmann reagent (0.442 g, 2.15 mmol) dissolved in MeOH (1 mL), powdered K$_2$CO$_3$ (0.370 g, 2.68 mmol) were stirred at 0° C. Following the general workup and flash chromatography (SiO$_2$, 10 g, 5% EtOAc/hexanes) alkyne 22 was obtained as a white solid (0.200 g, 47% yield over 3 steps); TLC $R_f$=0.2 (5% EtOAc/hexanes); mp 103.7-104° C.; $^1$H NMR (500 MHz, CDCl$_3$) δ 7.72 (m, 2H), 7.67 (m, 3H), 7.19 (d, J=7.9 Hz, 1H), 7.03 (s, 1H), 4.23 (q, J=7.0, 1H), 3.92 (s, 3H), 2.25 (d, J=2.4 Hz, 1H), 1.48 (d, J=7.0 Hz, 3H); $^{13}$C NMR (125 MHz, CDCl$_3$) δ 156.7, 145.8, 139.3, 132.7, 131.9. 128.6, 127.9, 119.9, 119.9, 119.1, 111.1, 109.5, 87.3, 69.9, 55.8, 25.4, 22.8; IR (neat cm$^{-1}$) 3285, 3069, 2935, 2221, 1604, 1488, 1393, 1225, 1024, 807, 657; HRMS (DART, M$_+$+H) m/z 262.1253 (calculated for C$_{18}$H$_{16}$NO, 262.1232).

4'-[3-(2,4-Diamino-6-ethyl-pyrimidin-5-yl)-1-methyl-prop-2-ynyl]-3'-methoxy-biphenyl-4-carbonitrile (32)

According to the general Sonogahisra coupling procedure, ethyl-iodopyrimidine (0.056 g, 0.21 mmol), CuI (0.006 g, 0.031 mmol, 15 mol %), Pd(PPh$_3$)$_2$Cl$_2$ (0.015 g, 0.021 mmol, 10 mol %) and alkyne 22 (0.084 g, 0.318 mmol) were reacted in DMF/Et$_3$N (1 mL each) at 70° C. for 12 h. After the mixture was cooled, dark reddish brown solution was concentrated and the product was purified by flash chromatography (SiO$_2$, 5 g, 2% MeOH/CHCl$_3$) followed by reverse phase flash chromatography (NH$_2$ capped SiO$_2$, 3 g, 100% CH$_2$Cl$_2$, 1% MeOH/CH$_2$Cl$_2$) to afford coupled pyrimidine 32 as a pale white powder (0.065 g, 78%); TLC $R_f$=0.2 (5% MeOH/CH$_2$Cl$_2$); mp 130.9-133.1° C.; $^1$H NMR (500 MHz, CDCl$_3$) δ 7.73-7.70 (m, 2H), 7.69-7.63 (m, 3H), 7.19 (dd, J=7.8, 1.7 Hz, 1H), 7.05 (d, J=1.7 Hz, 1H), 5.24 (s, 2H), 4.98 (s, 2H), 4.45 (q, J=7.0 Hz, 1H), 3.94 (s, 3H), 2.71 (q, J=7.6 Hz, 2H), 1.55 (d, J=7.0 Hz, 3H), 1.24 (t, J=7.6 Hz, 3H); $^{13}$C NMR (125 MHz, CDCl$_3$) δ 173.4, 164.5, 160.8, 156.8, 145.7, 139.3, 132.8, 132.5, 128.5, 127.9, 119.9, 119.1, 111.1, 109.6, 101.9, 90.8, 74.8, 55.6, 29.8, 26.9, 23.0, 12.7; IR (neat cm$^{-1}$) 3464, 3428, 3332, 3188, 3029, 2925, 2775, 2546, 1651, 1548, 1445, 1286, 1008, 735, 557; HRMS (DART, M$_+$+H) m/z 398.1983, (calculated for C$_{24}$H$_{24}$N$_5$O, 398.1981); HPLC (a) $t_R$=19.2 mins, 99.6%, (b) $t_R$=17.5 mins, 99.5%.

Example 3

Preparation of Compound 33

Compound 33, Carbamic acid 4'-[3-(2,4-diamino-6-ethyl-pyrimidin-5-yl)-1-methyl-prop-2-ynyl]-3'-methoxy-biphenyl-4-yl ester, of Reaction Scheme 1 was prepared as described.

3'-Methoxy-4'-(1-methyl-prop-2-ynyl)-biphenyl-4-ol (20)

According to the general procedure for homologation, methoxymethyl triphenylphosphonium chloride (4.71 g, 13.73 mmol) in dry THF (37 mL), NaO$_t$Bu (1.58 g, 16.5 mmol), ketone 11 as described in Example 1 (1.79 g, 5.49 mmol) in THF (7 mL) were stirred at 0° C. Following the general workup, the mixture of enol ethers (1.77 g, 5.00 mmol) in THF/H$_2$O (9:1, 17 mL) were hydrolyzed using Hg(OAc)$_2$ (4.8 g, 14.97 mmol) at room temperature. After the general extraction procedure, aldehyde (1.564 g, 4.65 mmol) in MeOH (20 mL), Ohira-Bestmann reagent (1.60 g, 8.4 mmol) dissolved (11 mL) in MeOH, powdered K$_2$CO$_3$ (1.337 g, 9.7 mmol) were stirred at 0° C. Following the general workup and flash chromatography (SiO$_2$, 30 g, 15% EtOAc/hexanes) O-THP alkyne was obtained as a pale white solid (0.84 g). Deprotection of O-THP alkyne was carried out by dissolving the protected alkyne (0.84 g, 2.5 mmol) in MeOH (150 mL) and cooled to 0° C. p-Toluenesulfonic acid (0.951 g, 2.5 mmol) was added and reaction allowed to warm to room temperature. The reaction was followed by TLC, diluted with water, neutralized with sat NaHCO$_3$ and extracted with ether. The organic extracts were washed with brine, dried over MgSO$_4$ and filtered. The filtrate was concentrated and purified by flash column chromatography (SiO$_2$, 30 g, 15% EtOAc/hexanes) to give the terminal acetylene 20 as a white solid (0.61 g, 43% yield over 4 steps); TLC R$_f$=0.3 (25% EtOAc/hexanes); mp 90.2-91° C.; $^1$H NMR (500 MHz, CDCl$_3$) δ 7.57 (d, J=7.9 Hz, 1H), 7.45 (d, J=8.6 Hz, 2H), 7.11 (dd, J=7.9, 1.7 Hz, 1H), 6.98 (d, J=1.6 Hz, 1H), 6.88 (d, J=8.6 Hz, 2H), 4.18 (qd, J=7.0, 2.4 Hz, 1H), 3.88 (s, 3H), 2.20 (d, J=2.5 Hz, 1H), 1.45 (d, J=7.0 Hz, 3H); $^{13}$C NMR (125 MHz, CDCl$_3$) δ 156.5, 155.3, 141.0, 134.3, 129.7, 128.6, 128.2, 119.4, 115.8, 109.3, 87.8, 69.5, 55.7, 25.3, 22.9; IR (neat cm$^{-1}$) 3334. 3300, 2938, 1606, 1494, 1218, 807, 633; HRMS (DART, M$_+$+H) m/z 253.1224 (calculated for C$_{17}$H$_{17}$O$_2$, 253.1229).

Carbamic acid 3'-methoxy-4'-(1-methyl-prop-2-ynyl)-biphenyl-4-yl ester (23)

To a 25 mL flame dried flask with stir bar cooled to room temperature was added alkyne 20 (0.115 g, 0.46 mmol) dissolved in anhydrous CH$_2$Cl$_2$. The reactant was cooled to 0° C. and chlorosulfonyl isocyanate (0.08 mL, 0.92 mmol) was added dropwise. After 15 min, the reaction mixture was brought to room temperature and followed by TLC. The reaction was quenched with water and extracted with ether. The organic extracts were washed with brine, dried over MgSO$_4$, and filtered. The filtrate was concentrated and purified by flash column chromatography (SiO$_2$, 7 g, 25% EtOAc/hexanes) to give the terminal acetylene 23 as a white solid (0.092 g, 68% yield): TLC R$_f$=0.1 (25% EtOAc/hexanes); mp 113.6-115.3° C.; $^1$H NMR (500 MHz, CDCl$_3$) δ 7.61 (d, J=7.8 Hz, 1H), 7.56 (d, J=8.5 Hz, 2H), 7.19 (d, J=8.5 Hz, 2H), 7.15 (dd, J=7.8, 1.4 Hz, 1H), 7.01 (d, J=1.7 Hz, 1H), 4.21 (qd, J=7.0, 2.3 Hz, 1H), 3.88 (s, 3H), 2.23 (d, J=2.4 Hz, 1H), 1.47 (d, J=7.0 Hz, 3H); $^{13}$C NMR (125 MHz, CDCl$_3$) δ 189.2, 156.4, 155.6, 150.3, 140.6, 138.9, 133.1, 130.3, 128.3, 128.2, 122.1, 119.7, 109.6, 87.7, 69.6, 60.6, 55.7, 25.3, 22.8, 21.2, 14.4; IR (neat cm$^{-1}$) 3423, 3308, 3268, 3199, 2969, 2341, 2105, 1698, 1606, 1494, 1378, 1213, 586; HRMS (DART, M$_+$+H) m/z 296.1300 (calculated for C$_{18}$H$_{18}$NO$_3$, 296.1287).

Carbamic acid 4'-[3-(2,4-diamino-6-ethyl-pyrimidin-5-yl)-1-methyl-prop-2-ynyl]-3'-methoxy-biphenyl-4-yl ester (33)

According to a general Sonogahisra coupling procedure, ethyl-iodopyrimidine (0.055 g, 0.21 mmol), CuI (0.008 g, 0.04 mmol, 21 mol %), Pd(PPh$_3$)$_2$Cl$_2$ (0.015 g, 0.021 mmol, 10 mol %) and alkyne 23 (0.092 g, 0.31 mmol) were reacted in DMF/Et$_3$N (1 mL each) at 60° C. for 12 h. After the mixture was cooled, dark reddish brown solution was concentrated and the product was purified by flash chromatography (SiO$_2$, 5 g, 2% MeOH/CHCl$_3$) to afford coupled pyrimidine 33 as a pale white powder (0.076 g, 84%) followed by reverse phase flash chromatography (NH$_2$ capped SiO$_2$, 3 g, 100% CH$_2$Cl$_2$, 1% MeOH/CH$_2$Cl$_2$) for biological evaluation: TLC R$_f$=0.07 (5% MeOH/CH$_2$Cl$_2$); $^1$H NMR (500 MHz, MeOD) δ 7.53 (d, J=7.8 Hz, 1H), 7.46 (d, J=8.6 Hz, 2H), 7.13 (dd, J=7.8, 1.60, 1H), 7.11 (d, J=1.3 Hz, 1H), 6.85 (d, J=8.6 Hz, 2H), 4.41 (q, J=6.9 Hz, 1H), 3.93 (s, 3H), 2.67 (q, J=7.6 Hz, 2H), 1.52 (d, J=7.0 Hz, 3H), 1.22 (t, J=7.6 Hz, 3H); $^{13}$C NMR (125 MHz, MeOD) δ 173.5, 166.1, 162.2, 158.3, 157.9, 142.7, 133.8, 130.9, 129.1, 128.9, 119.9, 116.7, 110.1, 103.2, 91.4, 74.9, 56.2, 30.4, 27.9, 23.4, 13.3; 6 IR (neat cm$^{-1}$) 3477, 3386, 3336, 3195, 2970, 2929, 2873, 2361, 2023, 1603, 1437, 1217, 1027, 813. HRMS (ESI, M$_+$+Na) m/z 455.1947 (calculated for C$_{24}$H$_{26}$N$_5$NaO$_3$, 455.1928); HPLC (a) t$_R$=6.8 mins, 98%, (b) t$_R$=8.2 mins, 98.7%.

Example 4

Preparation of Compound 34

Compound 34, 4'-[3-(2,4-Diamino-6-ethyl-pyrimidin-5-yl)-1-methyl-prop-2-ynyl]-3'-methoxy-biphenyl-4-carboxylic acid methyl ester, of Reaction Scheme 1 was prepared as described.

4'-Acetyl-3'-methoxy-biphenyl-4-carboxylic acid methyl ester (14)

According to the general Suzuki coupling procedure, ketone 7 (0.506 g, 2.21 mmol), 4-(methoxycarbonyl)phenylboronic acid (0.795 g, 4.42 mmol), Cs$_2$CO$_3$ (2.16 g, 6.63 mmol), Pd(PPh$_3$)$_2$Cl$_2$ (0.155 g, 0.22 mmol, 10% Pd) and anhydrous dioxane (6 mL) were heated at 80° C. for 14 h (overnight). Following the general workup and flash chromatography (SiO$_2$, 20 g, 15% EtOAc/hexanes) biaryl ketone 14 was obtained as a white solid (0.490 g, 78%): TLC R$_f$=0.4 (25% EtOAc/hexanes); mp 140.4142.6° C.; $^1$H NMR (500 MHz, CDCl$_3$) δ 8.09 (d, J=8.0 Hz, 2H), 7.81 (d, J=8.0 Hz, 1H), 7.63 (d, J=8.0 Hz, 2H), 7.20 (d, J=8.0 Hz, 1H), 7.14 (s, 1H), 3.97 (s, 3H), 3.91 (s, 3H), 2.62 (s, 3H); $^{13}$C NMR (125 MHz, CDCl$_3$) δ 199.3, 166.9, 159.5, 145.6, 144.7, 131.3, 130.3, 129.9, 127.5, 127.4, 119.8, 110.7, 55.8, 52.4, 32.1; IR (neat cm$^{-1}$) 2997, 2955, 2929, 2845, 2162, 1714, 1657, 1604, 1554, 1280, 1247, 831, 768. HRMS (DART, M$_+$+H) m/z 285.1111 (calculated for C$_{17}$H$_{17}$O$_4$, 285.1127).

3'-Methoxy-4'-(1-methyl-prop-2-ynyl)-biphenyl-4-carboxylic acid methyl ester (24)

According to general procedure for homologation, methoxymethyl triphenylphosphonium chloride (1.05 g, 3.06 mmol) in dry THF (9 mL), NaO$_t$Bu (0.367 g, 3.9 mmol), ketone 14 (0.434 g, 1.59 mmol) in THF (3 mL) were stirred at 0° C. Following the general workup, the mixture of enol ethers (0.214 g, 0.69 mmol) in THF/H$_2$O (9:1, 5 mL) were hydrolyzed using Hg(OAc)$_2$ (0.656 g, 2.1 mmol) at room temperature. After the general extraction procedure, aldehyde (0.194 g, 0.65 mmol) in MeOH (3 mL), Ohira-Bestmann reagent (0.224 g, 1.17 mmol) dissolved in MeOH (2 mL), powdered K$_2$CO$_3$ (0.188 g, 1.36 mmol) were stirred at 0° C. Following the general workup and flash chromatography (SiO$_2$, 7 g, 2% EtOAc/hexanes) alkyne 24 was obtained as a white solid (0.111 g, 25% yield over 3 steps); TLC $R_f$=0.3 (5% EtOAc/hexanes); mp 106-108.5° C.; $^1$H NMR (500 MHz, CDCl$_3$) δ 8.09 (d, J=8.1 Hz, 2H), 7.72-7.57 (m, 3H), 7.20 (d, J=7.7 Hz, 1H), 7.06 (s, 1H), 4.21 (q, J=5.0 Hz, 1H), 3.92 (s, 3H), 3.90 (s, 3H), 2.23 (d, J=2.0 Hz, 1H), 1.47 (d, J=7.0 Hz, 3H); $^{13}$C NMR (125 MHz, CDCl$_3$) δ 167.1, 156.5, 145.8, 140.1, 131.3, 130.2, 129.1, 128.4, 127.2, 119.9, 109.5, 87.5, 69.7, 55.7, 52.3, 25.4, 22.8; IR (neat cm$^{-1}$) 3255, 2970, 2950, 2929, 2108, 1698, 1605, 1430, 1393, 1104, 1281, 769, 676; HRMS (DART, M$_+$+H) m/z 295.1329 (calculated for C$_{19}$H$_{19}$O$_3$, 295.1334).

4'-[3-(2,4-Diamino-6-ethyl-pyrimidin-5-yl)-1-methyl-prop-2-ynyl]-3'-methoxy-biphenyl-4-carboxylic acid methyl ester (34)

According to a general Sonogahisra coupling procedure, ethyl-iodopyrimidine (0.061 g, 0.23 mmol), CuI (0.009 g, 0.05 mmol, 21 mol %), Pd(PPh$_3$)$_2$Cl$_2$ (0.016 g, 0.023 mmol, 10 mol %) and alkyne 24 (0.100 g, 0.34 mmol) were reacted in DMF/Et$_3$N (1 mL each) at 60° C. for 12 h. After the mixture was cooled, dark reddish brown solution was concentrated and the product was purified by flash chromatography (SiO$_2$, 5 g, 2% MeOH/CHCl$_3$) to afford coupled pyrimidine 34 as a pale white powder (0.077 g, 77%) followed by reverse phase flash chromatography (NH$_2$ capped SiO$_2$, 3 g, 100% CH$_2$Cl$_2$, 1% MeOH/CH$_2$Cl$_2$): TLC $R_f$=0.1 (5% MeOH/CH$_2$Cl$_2$); mp 168.2-170.8° C.; $^1$H NMR (500 MHz, CDCl$_3$) δ 8.08 (d, J=8.55 Hz, 2H), 7.64-7.60 (m, 3H), 7.21 (dd, J=7.8, 1.6 Hz, 1H), 7.08 (d, J=1.5 Hz, 1H), 5.15 (s, 2H), 4.84 (s, 2H), 4.43 (q, J=7.0 Hz, 1H), 3.93 (s, 3H), 3.92 (s, 3H), 2.70 (q, J=7.6 Hz, 2H), 1.54 (d, J=7.0 Hz, 3H), 1.23 (t, J=7.6 Hz, 3H); $^{13}$C NMR (126 MHz, CDCl$_3$) δ 173.5, 167.2, 164.5, 160.8, 156.7, 145.7, 140.2, 131.9, 130.3, 129.2, 128.3, 127.2, 120.0, 109.7, 102.1, 90.9, 74.7, 55.8, 52.4, 29.9, 26.9, 23.1, 12.8; IR (neat cm$^{-1}$) 3427, 3302, 3163, 2925, 2851, 2150, 1699, 1548, 1282, 771, 698, 505; HRMS (ESI, M$_+$+H) m/z 431.2081 (calculated for C$_{25}$H$_{27}$N$_4$O$_3$, 431.2078); HPLC (a) t$_R$=20.5 mins, 99.4%, (b) t$_R$=18.1 mins, 99.1%.

Example 5

Preparation of Compound 35

Compound 35, 5-[3-(4'-Dimethylamino-3-methoxy-biphenyl-4-yl)-but-1-ynyl]-6-ethyl-pyrimidine-2,4-diamine, of Reaction Scheme 1 was prepared as described.

1-(4'-Dimethylamino-3-methoxy-biphenyl-4-yl)-ethanone (15)

According to the general Suzuki coupling procedure, ketone 7 (0.50 g, 2.18 mmol), N,N-dimethylamine phenylboronic acid (0.43 g, 2.62 mmol), Cs$_2$CO$_3$ (2.13 g, 6.54 mmol), Pd(PPh$_3$)$_2$Cl$_2$ (0.15 g, 0.22 mmol, 10% Pd) and anhydrous dioxane (8 mL) were added to 50 mL screw cap pressure vessel. The mixture was stirred, degassed by purging with argon for 15 min and placed in an 80° C. oil bath for 12 h. Following the general workup and flash chromatography (SiO$_2$, 20 g, 50% EtOAc/Hexanes) ketone 15 was obtained as a yellow solid (0.42 g, 72%); TLC $R_f$=0.41 (20% EtOAc/Hexanes); mp 107.7-108.0° C.; $^1$H NMR (500 MHz, Chloroform-d) δ 7.80 (d, J=8.1 Hz, 1H), 7.52 (d, J=8.7 Hz, 2H), 7.17 (dd, J=8.1, 1.4 Hz, 1H), 7.10 (s, 1H), 6.78 (d, J=8.8 Hz, 2H), 3.96 (s, 3H), 3.00 (s, 6H), 2.62 (s, 3H); $^{13}$C NMR (125 MHz, CDCl$_3$) δ 199.2, 159.8, 150.8, 147.2, 131.3, 128.1, 125.6, 118.6, 112.7, 109.3, 55.7, 40.6, 32.1; IR (neat cm$^{-1}$) 2894, 2816, 1657, 1588, 1564, 807; HRMS (DART, M$_+$+H) m/z 270.1488 (calculated for C$_{17}$H$_{20}$NO$_2$, 270.1494).

3'-Methoxy-4'-(1-methyl-prop-2-ynyl)-biphenyl-4-yl)-dimethyl-amine (25)

According to a general procedure for homologation, methoxymethyl triphenylphosphonium chloride (0.67 g, 1.95 mmol) in dry THF (10 mL), NaO$_t$Bu (0.22 g, 2.34 mmol), ketone 15 (0.21 g, 0.78 mmol) in THF (3 mL) were stirred at 0° C. Following the general workup, the mixture of enol ethers (0.18 g, 0.62 mmol) in THF/H$_2$O (9:1, 10 mL) were hydrolyzed using Hg(OAc)$_2$ (0.30 g, 0.93 mmol) at room temperature. After the general extraction procedure, aldehyde (0.17 g, 0.62 mmol) in dry MeOH (6 mL), Ohira-Bestmann reagent (0.36 g, 1.86 mmol) dissolved in MeOH (2 mL), powdered K$_2$CO$_3$ (0.26 g, 1.86 mmol) were stirred at 0° C. Following the general workup and flash chromatography (SiO$_2$, 10 g, 15% EtOAc/Hexanes) alkyne 25 was obtained as a white solid (0.015 g, 6% yield over 3 steps); TLC $R_f$=0.52 (10% EtOAc/Hexanes); mp 60.8-61.1° C.; $^1$H NMR (500 MHz, Chloroform-d) δ 7.56 (d, J=7.9 Hz, 1H), 7.48 (d, J=8.9 Hz, 2H), 7.14 (dd, J=7.9, 1.7 Hz, 1H), 7.01 (d, J=1.6 Hz, 1H), 6.79 (d, J=8.7 Hz, 2H), 4.18 (qd, J=7.1, 2.6 Hz, 2H), 3.88 (s, 3H), 2.98 (s, 6H), 2.20 (d, J=2.5 Hz, 1H), 1.46 (d, J=7.1 Hz, 3H); $^{13}$C NMR (125 MHz, CDCl$_3$) δ 156.4, 150.2, 141.5, 129.5, 128.9, 128.0, 127.9, 118.9, 112.9, 108.9, 88.0, 69.4, 55.6, 40.8, 25.3, 22.9; IR (neat cm$^{-1}$) 3292, 2972, 2932, 1605, 1574, 1397, 804; HRMS (DART, M$_+$+H) m/z 280.1703 (calculated for C$_{19}$H$_{22}$NO, 280.1701).

5-[3-(4'-Dimethylamino-3-methoxy-biphenyl-4-yl)-but-1-ynyl]-6-ethyl-pyrimidine-2,4-diamine (35)

According to a general Sonogahisra coupling procedure, ethyl-iodopyrimidine (0.014 g, 0.05 mmol) CuI (0.002 g, 0.010 mmol, 20 mol %), Pd(PPh$_3$)$_2$Cl$_2$ (0.004 g, 0.005 mmol, 10 mol %) and alkyne 25 (0.015 g, 0.050 mmol) were reacted in DMF/Et$_3$N (0.5 mL/0.5 mL) at 60° C. for 6 h. After the mixture was cooled, dark reddish brown solution was concentrated and the product was purified by flash chromatography (SiO$_2$, 10 g, 100% EtOAc followed by 2% MeOH/CH$_2$Cl$_2$) followed by reverse phase flash chromatography (NH$_2$ capped SiO$_2$, 5 g, 100% CH$_2$Cl$_2$) to afford pyrimidine 35 as an off-white solid (9 mg, 43%); TLC $R_f$=0.22 (5% MeOH/CH$_2$Cl$_2$); mp 135.2-136.1° C.; $^1$H NMR (500 MHz, Chloroform-d) δ 7.51 (d, J=7.8 Hz, 1H), 7.47 (d, J=8.6 Hz, 2H), 7.14 (d, J=5.0 Hz, 1H), 7.03 (s, 1H), 6.78 (d, J=10.0 Hz, 2H), 5.24 (s, 2H), 5.01 (s, 2H), 4.40 (q, J=7.0 Hz, 1H), 3.90 (s, 3H), 2.98 (s, 6H), 2.71 (q, J=7.6 Hz, 2H), 1.53 (d, J=7.0 Hz, 3H), 1.25 (t, J=6.9 Hz, 3H); $^{13}$C NMR (125 MHz, CDCl$_3$) δ 164.7, 157.9, 156.6, 150.3, 141.9, 129.1, 128.7, 127.9, 119.0, 112.9, 109.2, 103.9, 92.0, 72.3, 55.7, 40.8, 28.1, 26.9, 22.7, 12.6; IR (neat cm$^{-1}$) 3310, 3172, 2925, 2873, 1603, 1570, 807; HRMS (ES, M$_+$+H) m/z 416.2442 (calculated for C$_{25}$H$_{30}$N$_5$O, 416.2445); HPLC was not obtained because of the instability of the compound. Biological activity was tested immediately after the synthesis.

Example 6

Preparation of Compound 46

Compound 46, 6-Ethyl-5-[3-(6-phenyl-pyridin-3-yl)-but-1-ynyl]-pyrimidine-2,4-diamine, of Reaction Scheme 2 was prepared as described.

1-(6-Phenyl-pyridin-3-yl)-ethanone (40)

5-acetyl-2-bromopyridine 38 (0.656 g, 3.28 mmol), phenylboronic acid (0.800 g, 6.56 mmol), $Na_2CO_3$ (0.243 g, 2.29 mmol), $Pd(PPh_3)_2Cl_2$ (0.115 g, 0.16 mmol, 5% Pd), acetonitrile (26 mL) and $H_2O$ (26 mL) were added to 50 mL screw cap pressure vessel. The mixture was stirred, degassed by purging with argon for 15 min, sealed and placed in an 80° C. oil bath for 14 h (overnight). The dark colored mixture was cooled and extracted with ether. The organic layer was filtered through a pad of celite, rinsed with ether, washed with brine, dried over $MgSO_4$ and filtered. The filtrate was concentrated and the residue purified by flash column chromatography ($SiO_2$, 20 g, 5% EtOAc/hexanes) to afford the coupled ketone 40 as a white solid (0.33 g, 52%): TLC $R_f$=0.4 (25% EtOAc/hexanes); mp 124.9126.2° C.; $^1H$ NMR (500 MHz, $CDCl_3$) δ 9.22 (d, J=2.0 Hz, 1H), 8.28 (dd, J=8.3, 2.2 Hz, 1H), 8.10-7.99 (m, 2H), 7.83 (d, J=8.3 Hz, 1H), 7.55-7.40 (m, 3H), 2.65 (s, 3H); $^{13}C$ NMR (125 MHz, $CDCl_3$) δ 196.6, 161.1, 150.2, 138.2, 136.7, 130.9, 130.4, 129.2, 127.6, 120.4, 26.9; IR (neat $cm^{-1}$) 3062, 2999, 2960, 2322, 1673, 1557, 1382, 1016, 736; HRMS (DART, $M_++H$) m/z 198.0906 (calculated for $C_{13}H_{12}NO$, 198.0919).

5-(1-Methyl-prop-2-ynyl)-2-phenyl-pyridine (43)

According to a general procedure for homologation, methoxymethyl triphenylphosphonium chloride (1.01 g, 2.94 mmol) in dry THF (9 mL), $NaO_tBu$ (0.353 g, 3.7 mmol), ketone 40 (0.290 g, 1.47 mmol) in THF (3 mL) were stirred at 0° C. Following the general workup, the mixture of enol ethers (0.298 g, 1.33 mmol) in $THF/H_2O$ (9:1, 5 mL) were hydrolyzed using $Hg(OAc)_2$ (1.272 g, 3.9 mmol) at room temperature. After the general extraction procedure, aldehyde (0.175 g, 0.83 mmol) in MeOH (4 mL), Ohira-Bestmann reagent (0.238 g, 1.24 mmol) dissolved in MeOH (2 mL), powdered $K_2CO_3$ (0.240 g, 1.74 mmol) were stirred at 0° C. Following the general workup and flash chromatography ($SiO_2$, 5 g, 2% EtOAc/hexanes) alkyne 43 was obtained as a white solid (0.102 g, 34% yield over 3 steps): TLC $R_f$=0.3 (5% EtOAc/hexanes); mp 90.3-92° C.; $^1H$ NMR (500 MHz, $CDCl_3$) δ 8.67 (d, J=2.3 Hz, 1H), 7.97-7.95 (m, 2H), 7.79 (dd, J=8.2, 2.3 Hz, 1H), 7.68 (d, J=8.2 Hz, 1H), 7.49-7.42 (m, 2H), 7.42-7.36 (m, 1H), 3.83 (qd, J=7.2, 2.5 Hz, 1H), 2.30 (d, J=2.5 Hz, 1H), 1.55 (d, J=7.2 Hz, 3H); $^{13}C$ NMR (125 MHz, $CDCl_3$) δ 156.3, 148.6, 139.3, 136.6, 135.3, 129.0, 128.9, 127.0, 120.5, 85.9, 71.1, 29.2, 24.2; IR (neat $cm^{-1}$) 3292, 2976, 2930, 2870, 2325, 2107, 1594, 1473, 1293, 1018, 841, 740, 693, 644; HRMS (DART, $M_++H$) m/z 208.1144 (calculated for $C_{15}H_{14}N$, 208.1126).

6-Ethyl-5-[3-(6-phenyl-pyridin-3-yl)-but-1-ynyl]-pyrimidine-2,4-diamine (46)

According to the general Sonogahisra coupling procedure, ethyl-iodopyrimidine (0.071 g, 0.27 mmol), CuI (0.011 g, 0.06 mmol, 21 mol %), $Pd(PPh_3)_2Cl_2$ (0.019 g, 0.03 mmol, 10 mol %) and alkyne 43 (0.061 g, 0.3 mmol) were reacted in $DMF/Et_3N$ (1 mL each) at 60° C. for 12 h. After the mixture was cooled, dark reddish brown solution was concentrated and the product was purified by flash chromatography ($SiO_2$, 5 g, 2% $MeOH/CHCl_3$) to afford coupled pyrimidine 46 as a pale white hygroscopic solid (0.070 g, 75%), followed by reverse phase flash chromatography ($NH_2$ capped $SiO_2$, 3 g, 100% $CH_2Cl_2$, 1% $MeOH/CH_2Cl_2$) for biological evaluation: TLC $R_f$=0.1 (5% $MeOH/CH_2Cl_2$); $^1H$ NMR (500 MHz, $CDCl_3$) δ 8.72 (d, J=2.1 Hz, 1H), 7.96 (d, J=7.2 Hz, 2H), 7.81 (dd, J=8.2, 2.3 Hz, 1H), 7.70 (d, J=8.1 Hz, 1H), 7.46 (dd, J=7.5, 7.5 Hz, 1H), 7.46 (dd, J=7.5, 7.5 Hz, 1H), 7.41-7.38 (m, 1H), 5.09 (s, 2H), 4.84 (s, 2H), 4.11 (q, J=7.1 Hz, 1H), 2.68 (q, J=7.6 Hz, 2H), 1.63 (d, J=7.1 Hz, 3H), 1.22 (t, J=7.6 Hz, 3H); $^{13}C$ NMR (125 MHz, $CDCl_3$) δ 173.9, 164.4, 160.9, 156.4, 148.6, 139.3, 137.3, 135.3, 129.1, 128.9, 127.1, 120.6, 100.6, 90.4, 76.2, 30.6, 29.9, 24.7, 12.7; IR (neat $cm^{-1}$) 3469, 3308, 3166, 2972, 2931, 1730, 1542, 1435, 1238, 1018, 739, 692; HRMS (ESI, $M_++H$) m/z 344.1865 (calculated for $C_{21}H_{21}N_5$, 344.1875); HPLC (a) $t_R$=6.9 mins, 99.5%, (b) $t_R$=7.1 mins, 99.2%.

Example 7

Preparation of Compound 47

Compound 47, 6-Ethyl-5-[3-(6-p-tolyl-pyridin-3-yl)-but-1-ynyl]-pyrimidine-2,4-diamine, of Reaction Scheme 2 was prepared as described.

1-(6-p-Tolyl-pyridin-3-yl)-ethanone (41)

According to the general Suzuki coupling of pyridine compounds, 5-acetyl-2-bromopyridine 38 (0.394 g, 1.97 mmol), 4-tolylboronic acid (0.535 g, 3.94 mmol), $Na_2CO_3$ (0.146 g, 1.38 mmol), $Pd(PPh_3)_2Cl_2$ (0.042 g, 0.06 mmol, 3% Pd), acetonitrile (7.8 mL), water (7.8 mL) were heated at 80° C. for 14 h (overnight). Following the general workup and flash chromatography ($SiO_2$, 20 g, 5% EtOAc/hexanes) coupled ketone was obtained as a white solid 41 (0.381 g, 92%); TLC $R_f$=0.4 (25% EtOAc/hexanes); mp 106-107.5° C.; $^1H$ NMR (500 MHz, $CDCl_3$) δ 9.19 (d, J=2.2 Hz, 1H), 8.24 (dd, J=8.3, 2.3 Hz, 1H), 7.95 (d, J=8.2 Hz, 2H), 7.79 (d, J=8.4 Hz, 1H), 7.29 (d, J=8.4 Hz, 2H), 2.63 (s, 3H), 2.40 (s, 3H); $^{13}C$ NMR (125 MHz, $CDCl_3$) δ 196.6, 161.0, 150.2, 140.5, 136.4, 135.5, 130.5, 129.8, 127.4, 26.8, 21.5; IR (neat $cm^{-1}$) 3024, 2911, 2853, 2042, 1671, 1589, 1555, 1371, 1279, 1141, 819, 762; HRMS (DART, $M_++H$) m/z 212.1093 (calculated for $C_{14}H_{14}NO$, 212.1075).

5-(1-Methyl-prop-2-ynyl)-2-p-tolyl-pyridine (44)

According to a general procedure for homologation, methoxymethyl triphenylphosphonium chloride (4.47 g, 3.61 mmol) in dry THF (10 mL), $NaO_tBu$ (0.434 g, 4.5 mmol), ketone 41 (0.381 g, 1.81 mmol) in THF (5 mL) were stirred at 0° C. Following the general workup, the mixture of enol ethers (0.418 g, 1.75 mmol) in $THF/H_2O$ (9:1, 6 mL) were hydrolyzed using $Hg(OAc)_2$ (1.670 g, 5.26 mmol) at room temperature. After the general extraction procedure, aldehyde (0.197 g, 0.87 mmol) in MeOH (4 mL), Ohira-Bestmann reagent (0.252 g, 1.31 mmol) dissolved in MeOH (2 mL), powdered $K_2CO_3$ (0.254 g, 1.84 mmol) were stirred at 0° C. Following the general workup and flash chromatography ($SiO_2$, 7 g, 2% EtOAc/hexanes) alkyne 44 was obtained as a pale yellow solid (0.140 g, 33% yield over 3 steps): TLC $R_f$=0.3 (5% EtOAc/hexanes); mp 84.1-84.2° C.; $^1H$ NMR (500 MHz, $CDCl_3$) δ 8.65 (d, J=2.3 Hz, 1H), 7.86 (d, J=8.2 Hz, 2H), 7.77 (dd, J=8.2, 2.3 Hz, 1H), 7.66 (d, J=8.2 Hz, 1H), 7.26 (d, J=7.9 Hz, 2H), 3.82 (qd, J=7.1, 2.5 Hz, 1H), 2.39 (s, 3H), 2.29 (d, J=2.5 Hz, 1H), 1.54 (d, J=7.2 Hz, 3H); $^{13}C$ NMR (125 MHz, $CDCl_3$) δ 156.3, 148.6, 139.1, 136.6, 136.3, 135.3, 129.7, 126.9, 120.2, 86.1, 71.0, 29.3, 24.2, 21.5; IR (neat $cm^{-1}$) 3214, 2973, 2928, 2867, 2109, 1679, 1474, 1386, 1293, 1087, 1014, 818, 764, 697, 534; HRMS (DART, $M_++H$) m/z 222.1303 (calculated for $C_{16}H_{16}N$, 222.1283).

6-Ethyl-5-[3-(6-p-tolyl-pyridin-3-yl)-but-1-ynyl]-pyrimidine-2,4-diamine (47)

According to a general Sonogahisra coupling procedure, ethyl-iodopyrimidine (0.059 g, 0.23 mmol), CuI (0.009 g, 0.05 mmol, 21 mol %), Pd(PPh$_3$)$_2$Cl$_2$ (0.016 g, 0.022 mmol, 10 mol %) and alkyne 44 (0.06 g, 0.27 mmol) were reacted in DMF/Et$_3$N (1 mL each) at 60° C. for 12 h. After the mixture was cooled, dark reddish brown solution was concentrated and the product was purified by flash chromatography (SiO$_2$, 5 g, 2% MeOH/CHCl$_3$) to afford coupled pyrimidine 47 as a pale white powder (0.063 g, 76%) followed by reverse phase flash chromatography (NH$_2$ capped SiO$_2$, 3 g, 100% CH$_2$Cl$_2$, 1% MeOH/CH$_2$Cl$_2$) for biological evaluation: TLC R$_f$=0.1 (5% MeOH/CH$_2$Cl$_2$); mp 144-146.1° C.; $^1$H NMR (500 MHz, CDCl$_3$) δ 8.74 (d, J=2.2 Hz, 1H), 7.91 (d, J=8.1 Hz, 2H), 7.82 (dd, J=8.2, 2.3 Hz, 1H), 7.71 (d, J=8.2 Hz, 1H), 7.30 (d, J=8.6 Hz, 2H), 5.25 (s, 2H), 5.07 (s, 2H), 4.13 (q, J=7.1 Hz, 1H), 2.72 (q, J=7.6 Hz, 2H), 2.42 (s, 3H), 1.66 (d, J=7.1 Hz, 3H), 1.26 (t, J=7.6 Hz, 3H); $^{13}$C NMR (125 MHz, CDCl$_3$) δ 173.9, 164.5, 161.1, 156.4, 148.5, 139.1, 136.9, 136.5, 135.2, 129.7, 126.9, 120.3, 100.6, 90.3, 76.2, 30.6, 29.9, 24.6, 21.5, 12.7; IR (neat cm$^{-1}$) 3459, 3319, 3152, 2973, 2933, 2873, 1542, 1443, 923, 819, 762; HRMS (ESI, M$_+$+H) m/z 358.2013 (calculated for C$_{22}$H$_{24}$N$_5$, 358.2026); HPLC (a) t$_R$=9.7 mins, 99.7%, (b) t$_R$=9.4 mins, 99.5%.

Example 8

Preparation of Compound 48

Compound 48, 6-Ethyl-5-[3-(2-phenyl-pyrimidin-5-yl)-but-1-ynyl]-pyrimidine-2,4-diamine, of Reaction Scheme 2 was prepared as described.

1-(2-Phenyl-pyrimidin-5-yl)-ethanone (42)

Ketone 39 (0.72 g, 4.6 mmol), phenylboronic acid (0.841 g, 6.9 mmol), Pd(OAc)$_2$ (0.041 g, 0.184 mmol, 4% Pd), PPh$_3$ (0.241 g, 0.92 mmol), sat. Na$_2$CO$_3$ (23 mL), anhydrous dioxane (30 mL) were added to 100 mL screw cap pressure vessel. The mixture was stirred, degassed by purging with argon for 15 min, sealed and placed in an 110° C. oil bath for 14 h. The dark colored mixture was cooled and extracted with ether. The organic layer was filtered through a pad of celite, rinsed with ether, washed with brine, dried over MgSO$_4$ and filtered. The filtrate was concentrated and the residue purified by flash column chromatography (SiO$_2$, 20 g, 5% EtOAc/hexanes) to afford the coupled ketone 42 as a white solid (0.66 g, 74%): TLC R$_f$=0.4 (25% EtOAc/hexanes); mp 154-156° C.; $^1$H NMR (500 MHz, CDCl$_3$) δ 9.23 (s, 2H), 8.49 (dd, J=8.1, 1.6 Hz, 2H), 7.72-7.36 (m, 3H), 2.61 (s, 3H); $^{13}$C NMR (125 MHz, CDCl$_3$) δ 195.2, 167.2, 157.5, 136.7, 132.1, 130.0, 128.9, 127.4, 26.8; IR (neat cm$^{-1}$) 3077, 3036, 2049, 1681, 1537, 1429, 1376, 1271, 954, 744, 688; HRMS (DART, M$_+$+H) m/z 199.0868 (calculated for C$_{12}$H$_{11}$N$_2$O, 199.0871).

5-(1-Methyl-prop-2-ynyl)-2-phenyl-pyrimidine (45)

According to a general procedure for homologation, methoxymethyl triphenylphosphonium chloride (2.3 g, 6.62 mmol) in dry THF (18 mL), NaO$_t$Bu (0.797 g, 8.3 mmol), ketone 42 (0.655 g, 3.31 mmol) in THF (6 mL) were stirred at 0° C. Following the general workup, the mixture of enol ethers (0.398 g, 1.76 mmol) in THF/H$_2$O (9:1, 6 mL) were hydrolyzed using Hg(OAc)$_2$ (1.680 g, 5.28 mmol) at room temperature. After the general extraction procedure, aldehyde (0.300 g, 1.41 mmol) in MeOH (4 mL), Ohira-Bestmann reagent (0.407 g, 2.12 mmol) dissolved in MeOH (2 mL), powdered K$_2$CO$_3$ (0.410 g, 2.96 mmol) were stirred at 0° C. Following the general workup and flash chromatography (SiO$_2$, 5 g, 5% EtOAc/hexanes) alkyne 45 was obtained as a white solid (0.066 g, 10% yield over 3 steps): TLC R$_f$=0.3 (5% EtOAc/hexanes); mp 75.4-76.7° C.; $^1$H NMR (500 MHz, CDCl$_3$) δ 8.82 (s, 2H), 8.60-8.21 (m, 2H), 7.48-7.46 (m, 3H), 3.82 (qd, J=7.1, 2.5 Hz, 1H), 2.34 (d, J=2.5 Hz, 1H), 1.57 (d, J=7.2 Hz, 3H); $^{13}$C NMR (125 MHz, CDCl$_3$) δ 163.7, 156.1, 137.6, 133.3, 130.9, 128.8, 128.3, 84.6, 71.9, 27.4, 23.8; IR (neat cm$^{-1}$) 3205, 3059, 2978, 2934, 1584, 1547, 1425, 1296, 1175, 1094, 1069, 749, 692, 651; HRMS (DART, M$_+$+H) m/z 209.1103 (calculated for C$_{14}$H$_{13}$N$_2$, 209.1079).

6-Ethyl-5-[3-(2-phenyl-pyrimidin-5-yl)-but-1-ynyl]-pyrimidine-2,4-diamine (48)

According to a general Sonogahisra coupling procedure, ethyl-iodopyrimidine (0.105 g, 0.4 mmol), CuI (0.028 g, 0.08 mmol, 21 mol %), Pd(PPh$_3$)$_2$Cl$_2$ (0.028 g, 0.04 mmol, 10 mol %) and alkyne 45 (0.123 g, 0.6 mmol) were reacted in DMF/Et$_3$N (1.3 mL each) at 60° C. for 12 h. After the mixture was cooled, dark reddish brown solution was concentrated and the product was purified by flash chromatography (SiO$_2$, 5 g, 2% MeOH/CHCl$_3$) to afford coupled pyrimidine 48 as a pale white powder (0.099 g, 71%) followed by reverse phase flash chromatography (NH$_2$ capped SiO$_2$, 3 g, 100% CH$_2$Cl$_2$, 1% MeOH/CH$_2$Cl$_2$) for biological evaluation: TLC R$_f$=0.1 (5% MeOH/CH$_2$Cl$_2$); mp 161.3-162.8° C.; $^1$H NMR (500 MHz, CDCl$_3$) δ 8.84 (s, 2H), 8.62-8.02 (m, 2H), 7.88-7.37 (m, 3H), 5.16 (s, 2H), 4.98 (s, 2H), 4.10 (q, J=7.1 Hz, 1H), 2.67 (q, J=7.6 Hz, 2H), 1.65 (d, J=7.2 Hz, 3H), 1.22 (t, J=7.6 Hz, 3H); $^{13}$C NMR (12 MHz, CDCl$_3$) δ 174.1, 164.4, 163.8, 161.1, 156.1, 137.5, 133.9, 130.9, 128.8, 128.3, 99.2, 89.9, 29.9, 28.7, 24.3, 12.7; IR (neat cm$^{-1}$) 3401, 3312, 3159, 2970, 2933, 2871, 2222, 1623, 1563, 1427, 802, 740, 687; HRMS (ESI, M$_+$+H) m/z 345.1817 (calculated for C$_{20}$H$_{21}$N$_6$, 345.1822); HPLC (a) t$_R$=6.7 mins, 99.6%, (b) t$_R$=7.6 mins, 99.6%

Example 9

Crystallization and Structure Determination

*C. glabrata* and *C. albicans* DHFR were expressed and purified as described previously (Liu et al, Structure-guided development of efficacious antifungal agents targeting *Candida glabrata* dihydrofolate reductase. *Chem. Biol.*, 15:990-996 (2008); Paulsen et al, A., Crystal structures of *Candida albicans* dihydrofolate reductase bound to propargyl-linked antifolates reveal the flexibility of active site residues critical for ligand potency and selectivity, *Chem. Biol. Drug Des.*, 78:505-512 (2011); Paulsen et al, In vitro biological activity and structural analysis of 2,4-diamino-5-(2'-arylpropargyl) pyrimidine inhibitors of *Candida albicans, Bioorg. Med. Chem.*, 17:4866-4872 (2009)). Crystallization of the protein with ligand also followed previously described procedures (Paulsen et al 2011). Data were collected at Brookhaven National Laboratory, beamline X4A (CaDHFR) or X4C (CgDHFR). Molecular replacement was used to determine all three structures. Initial phase information was obtained using Phaser; electron density and model building used Coot. Refinement was carried out with Refmac 5 as part of the CCP4 package. Procheck was used to assess model quality.

Example 10

Enzyme Activity

Enzyme inhibition was determined by monitoring the consumption of NADPH at 340 nm for one minute. Reactions were performed with 20 mM TES pH 7.0, 50 mM KCl, 10 mM 2-mercaptoethanol, 0.5 mM EDTA and 1 mg/mL bovine serum albumin. Saturating concentrations of cofactor (100 µM NADPH) and substrate (100 µM dihydrofolate) were used with a limiting concentration of enzyme. All assays were conducted in triplicate at 25° C.

Antifungal Activity

Stock cultures of C. albicans (strain SC5314) or C. glabrata (strain NCCLS84), thawed from storage in 50% glycerol at −80° C., were streaked on YM agar plates and grown at 37° C. for 48 hours. Isolated colonies from the plate were suspended in 100 mL of glucose-salt-biotin (GSB) media containing ammonia chloride (2 g), potassium phosphate (0.35 g), magnesium sulfate (0.24 g), sodium citrate (0.3 g), piperazine-N,N'-bis[2-ethanesulfonic acid] (3.4 g), biotin (40 mg) and glucose (20 g) in 1 L of water at a final pH of 7.1. Strain SC5314 was grown at 25° C. for 18 hours (30 C for 24-36 hours for 5314), strain NCCLS84 was grown at 37° C. for 48-62 hours. An aliquot was removed from the shake flask culture, diluted to between $1\times10^5$ and $1\times10^6$ cells/mL in GSB media, and added to 96 well test plates (100 µL per well) containing test compounds dispensed in DMSO (1 µL). Amphotericin B and itraconazole were used as controls. C. albicans cell viability was determined by the addition of Alamar Blue (10 µL) to each well after a 24 hour incubation period. Antifungal activity was determined by observing the shift of maximum absorbance of Alamar Blue 123 from 570 nm to 600 nm indicating the minimum inhibitory concentration (MIC) of the compound under investigation. NCCLS84 has a much slower rate of metabolism than C. albicans strains and therefore Alamar blue could not be used to detect cell viability in a reasonable time frame (<24 hours). The XTT Cell Proliferation kit (ATCC) was used as an alternative. Tetrazolium dye, XTT, along with an electron activating reagent (50 µL) was added to 96 well plates and incubated for 24 hours at 37° C. Cell viability is indicated by a color change from a dark orange to a bright orange color that can be detected at 475-550 nM.

Kinetic Solubility

Compounds were initially dissolved as 20 µg/ml dimethyl sulfoxide (DMSO) solutions and diluted in filtered water in the presence or absence of 200 µg/ml methylcellulose (METHOCEL A4M; Dow Corning, Midland, Mich.). Final concentration of DMSO of all samples is 0.2%. All samples were incubated at room temperature for 30 min and centrifuged for 10 min at 15,000 rpm. Supernatant of the samples were analyzed by reversed phase HPLC. The mobile phase consisted of 50% acetonitrile (ACN) and 50% potassium phosphate buffer (50 mM, pH 7.0), using an isocratic flow rate of 1.5 ml/min. Solubility was determined as the maximal concentration for which absorption is linearly related to the log of the concentration.

TABLE 1

| Compound | $IC_{50}$ CgDHFR | $IC_{50}$ CaDHFR | $IC_{50}$ hDHFR | MIC C. glabrata (µg/mL) | MIC C. albicans (µg/mL) | $IC_{50}$ Human MCF-10 (µM) |
|---|---|---|---|---|---|---|
| 30 | 15 | 39 | 136 | 3.1 | NA[5] | 148 |
| 32 | 18 | 50 | 477 | 7.5 | 3.1 | 50 |
| 33 | 8 | 18 | 170 | 6.3 | NA | ND |
| 34 | 9 | 46 | 49 | 7.5 | 6.25 | 96 |
| 35 | 15 | 64 | 147 | 25 | NA | ND |
| 46 | 23 | 55 | 688 | 0.78 | 0.39 | ND |
| 47 | 27 | 49 | 625 | 0.2 | 0.39 | ND |
| 48 | 22 | 37 | 180 | 0.78 | 0.19 | 216 |

Those compounds substituted with hydrophobic functionality at the 4-position of the distal C-ring (such as 32) possess significant antifungal activity against C. albicans with MIC values ranging from 1.8-7.5 µg/mL. Excitingly, compounds 46-48 display a striking improvement in antifungal activity against both species (MIC=0.2-0.78 µg/mL). Additionally, compounds 46 and 47 are highly selective for the fungal enzymes (13-30-fold). In contrast to the distal pyridines, incorporation of pyridine in the B-ring (compounds 46 and 47) did not provide a significant increase in solubility (20 and 15 µg/mL, respectively). However, installation of the much more polar pyrimidine group (48) increased solubility to a very good level (60 µg/mL).

The shape and distribution of polar functionality in the compounds significantly impacts the C. glabrata and C. albicans antifungal activity despite the enzyme inhibitory potency. One hypothesis for these changes in activity could relate to differences in permeability. While membrane permeability is generally thought to be related to the hydrophobicity of the compounds, the dependence on the shape of the compounds may relate to a capacity to reach the intracellular target either because the compound fails to penetrate or becomes sequestered in the unique cell wall of C. albicans. The cell wall of C. albicans possesses more than 20 cell wall proteins covalently attached to the skeletal layer and tightly packed together, thus providing the organism with a protective protein coat and also limiting permeability. Cell wall proteins also tend to form phosphodiester linkages via carbohydrate side chains, giving the surface a net negative charge. C. glabrata is also known to express cell wall proteins, but much less is known about the composition of these proteins in the cell wall. One working hypothesis is that in situations where a concentration of polar functionality is symmetrically distributed, the compound may have strong, non-selective binding to the cell wall and hence, poor permeability. In contrast, compounds such as compounds 46, 47 and 48 are amphipathic in their distribution of polar functionality, which may limit their sequestration and increase their permeability. The differences in activity between C. albicans and C. glabrata may relate to differences in the composition of their cell walls.

Herein we describe a significant advance in the development of propargyl-linked antifolates targeting fungal pathogens. This work has identified a new generation of analogs that are highly potent inhibitors of the DHFR enzymes as well as the growth of both C. albicans and C. glabrata. We have shown that the shape and exposed polar functionality of the compounds strongly affects the antifungal activity. These compounds may be used for further development of antifungal antifolates as well as tools to probe the differences in cell walls of different species of Candida.

Example 11

This example demonstrates preparation of additional compounds of Formula IA using the following reaction scheme:

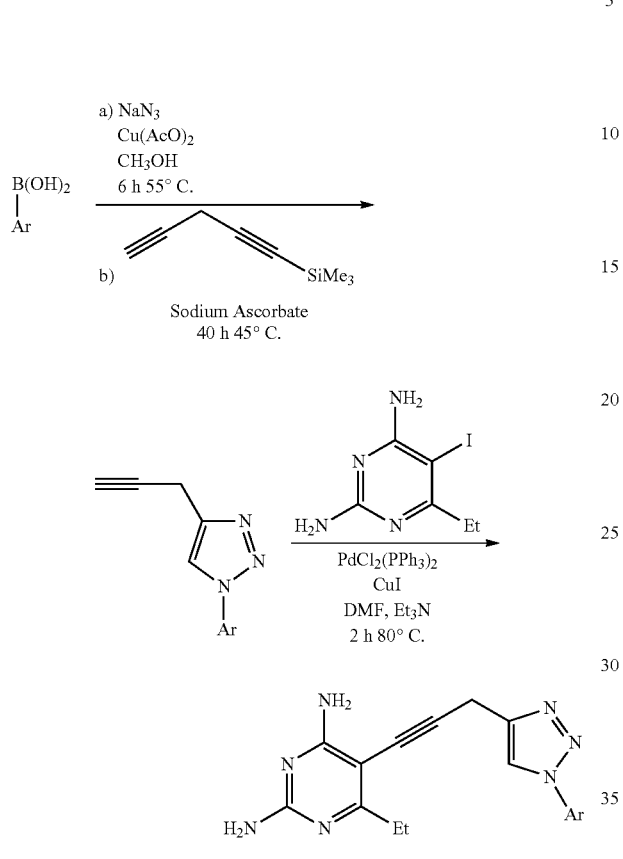

Aryl boronic acid (1.0 equiv), sodium azide (1.15 equiv) and copper(II) acetate (0.1 equiv) was dissolved in methanol (5 mL per mmol aryl boronic acid) and stirred at 55° C. for 6 hours in an round bottom under aerobic conditions. Reaction was allowed to cool to below 45° C. then 1-trimethylsilyl-1,4-pentadiyne (2.0 equiv) and 0.5M aqueous sodium ascorbate solution (0.1 equiv) were added, the reaction was then placed under argon and stirred at 45° C. for 40 hours. The reaction was allowed to cool to RT, then ammonium hydroxide (5 mL per mmol aryl boronic acid) and dichloromethane (5 mL per mmol aryl boronic acid) were added and the reaction was stirred 15 minutes at RT. The layers were separated; the aqueous was extracted with dichloromethane. The organic were combined, dried with sodium sulfate, concentrated, and then isolated via column chromatography on silica.

6-ethyl-5-iodopyrimidine-2,4-diamine (1.0 equiv), triazole alkyne (1.2 equiv), copper iodide (0.1 equiv) and bis(triphenylphosphine)palladium(II) dichloride (0.1 equiv) were purged with argon followed by the addition of degassed triethylamine (5 mL per mmol iodopyrimidine) and degassed DMF (5 mL per mmol iodopyrimidine), the vessel was sealed and stirred at 80° C. for 2 hours. The reaction was cooled to RT, diluted with EtOAc, then concentrated onto silica and purified by column chromatography on silica.

A. 6-ethyl-5-(3-(1-phenyl-1H-1,2,3-triazol-4-yl)prop-1-ynyl)pyrimidine-2,4-diamine

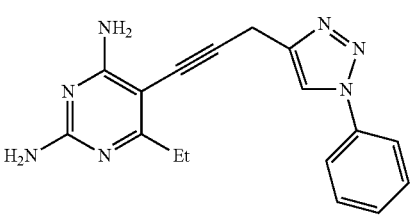 [SMILES: CCc1nc(N)nc(N)c1C#CCc1cn(-c2ccccc2)nn1]

1-phenyl-4-(prop-2-ynyl)-1H-1,2,3-triazole was produced in 23% yield.

6-ethyl-5-(3-(1-phenyl-1H-1,2,3-triazol-4-yl)prop-1-ynyl)pyrimidine-2,4-diamine was produced in 17% yield.

$^1$H NMR (300 MHz, CDCl$_3$): δ=1.24 (t, J=7.6 Hz, 3H), 2.69 (q, J=7.6 Hz, 2H), 4.06 (s, 2H), 7.47 (d, J=7.4 Hz, 1H), 7.55 (t, J=7.5 Hz, 2H), 7.73 (d, J=7.8 Hz, 2H), 7.95 (s, 1H).

B. Methyl 4-(4-(3-(2,4-diamino-6-ethylpyrimidin-5-yl)prop-2-ynyl)-1H-1,2,3-triazol-1-yl)benzoate

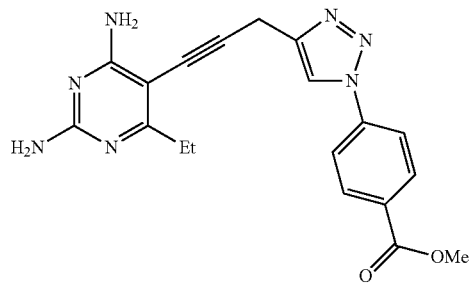 [SMILES: CCc1nc(N)nc(N)c1C#CCc1cn(-c2ccc(C(=O)OC)cc2)nn1]

methyl 4-(4-(prop-2-ynyl)-1H-1,2,3-triazol-1-yl)benzoate was produced in 13% yield.

methyl 4-(4-(3-(2,4-diamino-6-ethylpyrimidin-5-yl)prop-2-ynyl)-1H-1,2,3-triazol-1-yl)benzoate was produced in 15% yield.

$^1$H NMR (300 MHz, CDCl$_3$): δ=1.25 (t, J=7.5 Hz, 3H), 2.69 (q, J=7.5 Hz, 2H), 3.97 (s, 3H), 4.08 (s, 2H), 4.90 (br s, 2H), 5.4 (br s, 2H), 7.86 (d, J=8, 7 Hz, 2H), 8.00 (s, 1H), 8.21 (d, J=8.7 Hz, 2H).

C. 6-ethyl-5-(3-(1-(3,4,5-trifluorophenyl)-1H-1,2,3-triazol-4-yl)prop-1-ynyl)pyrimidine-2,4-diamine

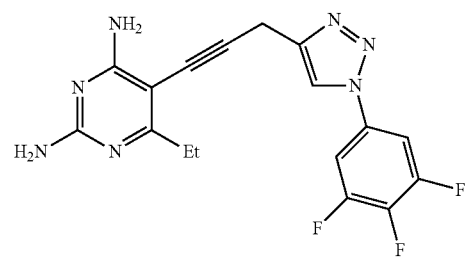 [SMILES: CCc1nc(N)nc(N)c1C#CCc1cn(-c2cc(F)c(F)c(F)c2)nn1]

4-(prop-2-ynyl)-1-(3,4,5-trifluorophenyl)-1H-1,2,3-triazole was produced in 40% yield.

6-ethyl-5-(3-(1-(3,4,5-trifluorophenyl)-1H-1,2,3-triazol-4-yl)prop-1-ynyl)pyrimidine-2,4-diamine was produced in 24% yield.

$^1$H NMR (300 MHz, CDCl$_3$): δ=1.24 (t, J=7.7 Hz, 3H), 2.69 (q, J=7.6 Hz, 2H), 4.06 (s, 2H), 4.86 (br s, 2H), 5.33 (br s, 2H), 7.46 (t, J=6.7 Hz, 2H), 7.88 (s, 1H).

D. 6-ethyl-5-(3-(1-(4-(trifluoromethyl)phenyl)-1H-1,2,3-triazol-4-yl)prop-1-ynyl)pyrimidine-2,4-diamine

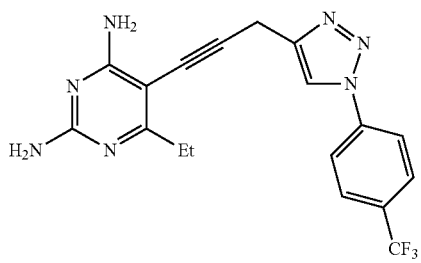 [SMILES: CCc1nc(N)nc(N)c1C#CCc1cn(-c2ccc(C(F)(F)F)cc2)nn1]

4-(prop-2-ynyl)-1-(4-(trifluoromethyl)phenyl)-1H-1,2,3-triazole was produced in 42% yield.

6-ethyl-5-(3-(1-(4-(trifluoromethyl)phenyl)-1H-1,2,3-triazol-4-yl)prop-1-ynyl)pyrimidine-2,4-diamine was produced in 38% yield.

$^1$H NMR (300 MHz, CDCl$_3$): δ=1.25 (t, J=7.5 Hz, 3H), 2.70 (q, J=7.6 Hz, 2H), 4.09 (s, 2H), 4.89 (br s, 2H), 5.38 (br s, 2H), 7.81 (d, J=8.6 Hz, 2H), 7.90 (d, J=8.5 Hz, 2H), 8.00 (s, 1H).

E. 5-(3-(1-(2,4-dimethylphenyl)-1H-1,2,3-triazol-4-yl)prop-1-ynyl)-6-ethylpyrimidine-2,4-diamine

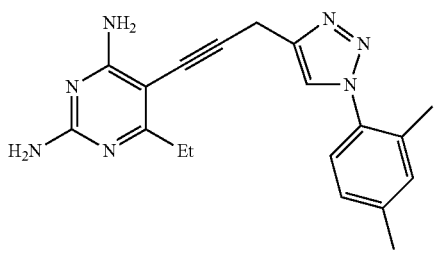 [SMILES: CCc1nc(N)nc(N)c1C#CCc1cn(-c2ccc(C)cc2C)nn1]

1-(2,4-dimethylphenyl)-4-(prop-2-ynyl)-1H-1,2,3-triazole was produced in 14% yield.

5-(3-(1-(2,4-dimethylphenyl)-1H-1,2,3-triazol-4-yl)prop-1-ynyl)-6-ethylpyrimidine-2,4-diamine was produced in 23% yield.

$^1$H NMR (300 MHz, CDCl$_3$): δ=1.23 (t, J=7.6 Hz, 3H), 2.18 (s, 3H), 2.40 (s, 3H), 2.69 (q, J=7.5 Hz, 2H), 4.07 (s, 2H), 5.12 (br s, 2H), 5.61 (br s, 2H), 7.10-7.22 (m, 3H), 7.64 (s, 1H).

Example 12

Additional compounds were prepared according to the following reaction scheme:

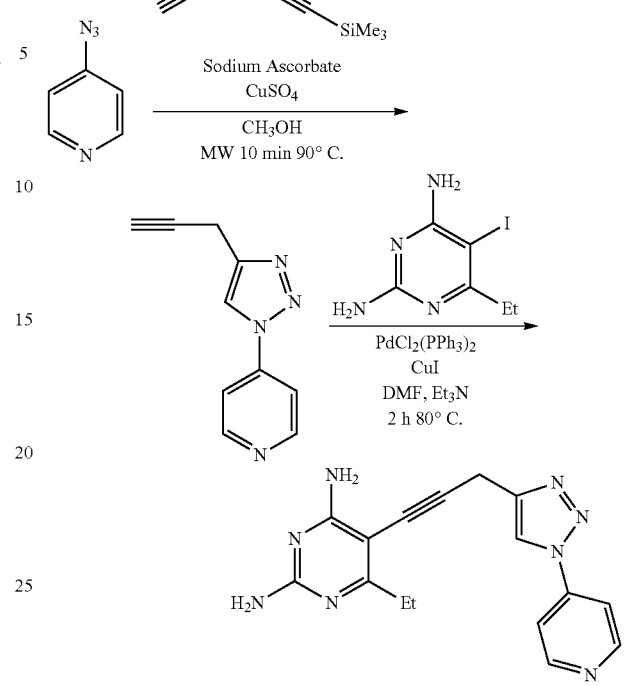

To a microwave vial was added 4-azidopyridine (1 equiv), 1-trimethylsilyl-1,4-pentadiyne (2.0 equiv), 1.0 M aqueous copper(II) sulfate (1 equiv), 0.5M aqueous sodium ascorbate solution (1 equiv) and methanol (1 mL per mmol 4-azidopyridine). Contents were sealed and heated to 90° C. for 10 in a microwave reactor. The reaction was allowed to cool to RT, then ammonium hydroxide (5 mL per mmol 4-azidopyridine) and dichloromethane (5 mL per mmol 4-azidopyridine) were added and the reaction was stirred 15 minutes at RT. The layers were separated; the aqueous was extracted with dichloromethane. The organic were combined, dried with sodium sulfate, concentrated, and then isolated via column chromatography on silica.

6-ethyl-5-iodopyrimidine-2,4-diamine (1.0 equiv), triazole alkyne (1.2 equiv), copper iodide (0.1 equiv) and bis(triphenylphosphine)palladium(II) dichloride (0.1 equiv) were purged with argon followed by the addition of degassed triethylamine (5 mL per mmol iodopyrimidine) and degassed DMF (5 mL per mmol iodopyrimidine), the vessel was sealed and stirred at 80° C. for 2 hours. The reaction was cooled to RT, diluted with EtOAc, then concentrated onto silica and purified by column chromatography on silica.

6-ethyl-5-(3-(1-(pyridin-4-yl)-1H-1,2,3-triazol-4-yl)prop-1-ynyl)pyrimidine-2,4-diamine

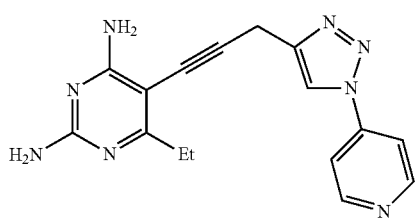 [SMILES: CCc1nc(N)nc(N)c1C#CCc1cn(-c2ccncc2)nn1]

4-(4-(prop-2-ynyl)-1H-1,2,3-triazol-1-yl)pyridine was produced in 16% yield.

6-ethyl-5-(3-(1-(pyridin-4-yl)-1H-1,2,3-triazol-4-yl)prop-1-ynyl)pyrimidine-2,4-diamine was produced in 19.3% yield following the general procedure.

$^1$H NMR (300 MHz, CDCl$_3$): δ=1.25 (t, J=7.6 Hz, 3H), 2.70 (q, J=7.6 Hz, 2H), 4.09 (s, 2H), 4.92 (br s, 2H), 5.38 (br s, 2H), 7.72 (d, J=6.0 Hz, 2H), 8.05 (s, 1H), 8.79 (d, J=5.6 Hz, 2H).

Example 13

Additional compounds were prepared according to the following reaction scheme:

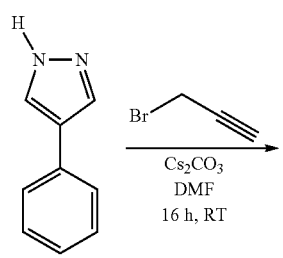

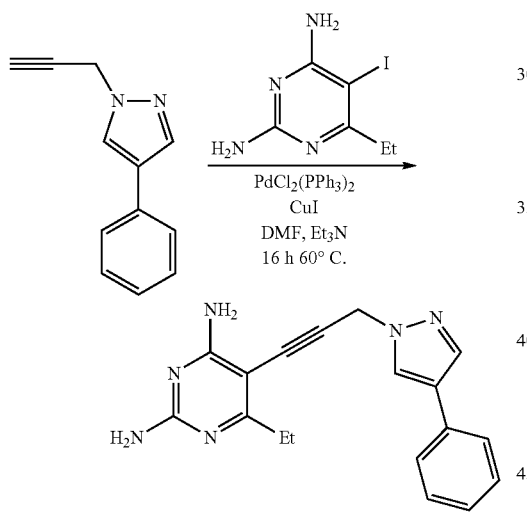

4-phenyl-1H-pyrazole (1.0 equiv), cesium carbonate (1.3 equiv) were dissolved in DMF (2 mL per mmol 4-phenyl-1H-pyrazole) followed by addition of propargyl bromide (1.1 equiv) and the mixture was stirred at RT for 5 hours. The mixture was diluted with EtOAc, washed with water and sat. aqueous sodium chloride, dried with sodium sulfate and concentrated. Product was isolated via column chromatography on silica.

6-ethyl-5-iodopyrimidine-2,4-diamine (1.0 equiv), 4-phenyl-1-(prop-2-ynyl)-1H-pyrazole (1.2 equiv), copper iodide (0.1 equiv) and bis(triphenylphosphine)palladium(II) dichloride (0.1 equiv) were purged with argon followed by the addition of degassed triethylamine (5 mL per mmol iodopyrimidine) and degassed DMF (5 mL per mmol iodopyrimidine), the vessel was sealed and stirred at 60° C. for 16 hours. The reaction was cooled to RT, diluted with EtOAc, then concentrated onto silica and purified by column chromatography on silica.

6-ethyl-5-(3-(4-phenyl-1H-pyrazol-1-yl)prop-1-ynyl)pyrimidine-2,4-diamine

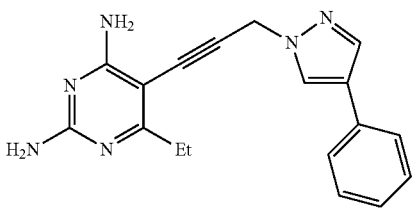 [SMILES: CCc1nc(N)nc(N)c1C#CCn1cc(-c2ccccc2)cn1]

4-phenyl-1-(prop-2-ynyl)-1H-pyrazole was produced in 72% yield.

6-ethyl-5-(3-(4-phenyl-1H-pyrazol-1-yl)prop-1-ynyl)pyrimidine-2,4-diamine was produced in 6% yield.

$^1$H NMR (300 MHz, CDCl$_3$): δ=1.23 (t, J=7.5 Hz, 3H), 2.68 (q, J=7.5 Hz, 2H), 5.07 (br s, 2H), 5.24 (s, 2H), 5.43 (br s, 2H), 7.23 (t, J=7.4 Hz, 1H), 7.36 (t, J=7.4 Hz, 2H), 7.48 (d, J=7.4 Hz, 2H), 7.83 (s, 1H), 7.86 (s, 1H).

Example 14

Additional compounds were prepared according to the following reaction scheme:

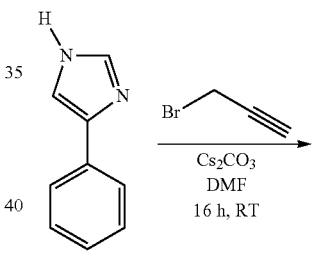

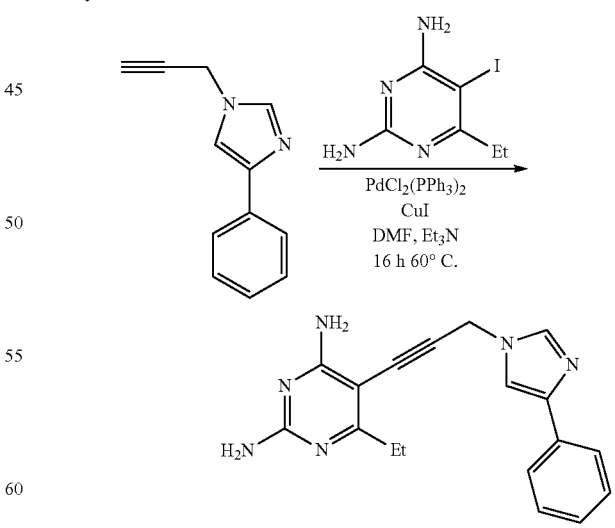

4-phenyl-1H-pyrazole (1.0 equiv), cesium carbonate (1.3 equiv) were dissolved in DMF (2 mL per mmol 4-phenyl-1H-pyrazole) followed by addition of propargyl bromide (1.1 equiv) and the mixture was stirred at RT for 5 hours. The mixture was diluted with EtOAc, washed with water and sat. aqueous sodium chloride, dried with sodium sulfate and concentrated. Product was isolated via column chromatography on silica.

6-ethyl-5-iodopyrimidine-2,4-diamine (1.0 equiv), 4-phenyl-1-(prop-2-ynyl)-1H-pyrazole (1.2 equiv), copper iodide (0.1 equiv) and bis(triphenylphosphine)palladium(II) dichloride (0.1 equiv) were purged with argon followed by the addition of degassed triethylamine (5 mL per mmol iodopyrimidine) and degassed DMF (5 mL per mmol iodopyrimidine), the vessel was sealed and stirred at 60° C. for 16 hours. The reaction was cooled to RT, diluted with EtOAc, then concentrated onto silica and purified by column chromatography on silica.

6-ethyl-5-(3-(4-phenyl-1H-imidazol-1-yl)prop-1-ynyl)pyrimidine-2,4-diamine

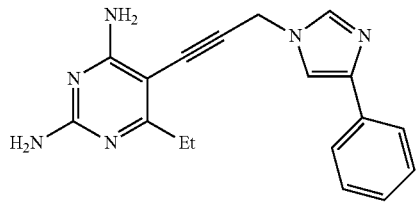 [SMILES: CCc1nc(N)nc(N)c1C#CCn1cnc(-c2ccccc2)c1]

4-phenyl-1-(prop-2-ynyl)-1H-imidazole was produced in 72% yield.

6-ethyl-5-(3-(4-phenyl-1H-imidazol-1-yl)prop-1-ynyl)pyrimidine-2,4-diamine was produced in 5% yield.

$^1$H NMR (300 MHz, CDCl$_3$): δ=1.20 (t, J=7.6 Hz, 3H), 2.68 (q, J=7.7 Hz, 2H), 5.06 (s, 2H), 5.55 (br s, 2H), 5.68 (br s, 2H), 7.23-7.40 (m, J=7.4 Hz, 4H), 7.69 (s, 2H), 7.78 (d, J=7.4 Hz, 2H).

Example 15

Additional compounds are prepared according to these reaction schemes via the indicated intermediates:

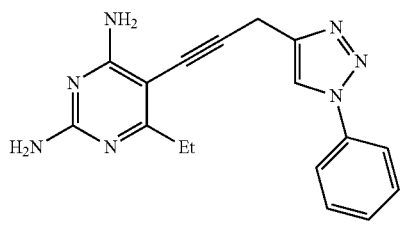

6-ethyl-5-(3-(1-phenyl-1H-1,2,3-triazol-4-yl)prop-1-ynyl)pyrimidine-2,4-diamine
Molecular Weight: 319.36

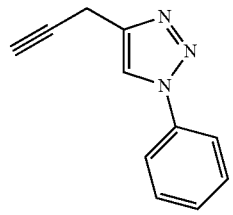

1-phenyl-4-(prop-2-ynyl)-1H-1,2,3-triazol

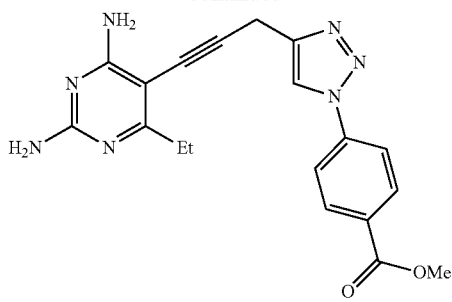

methyl-4-(4-(3-(2,4-diamino-6-ethylpyrimidin-5-yl)prop-2-ynyl)-1H-1,2,3-triazol-1-yl)benzoate
Molecular Weight: 377.40

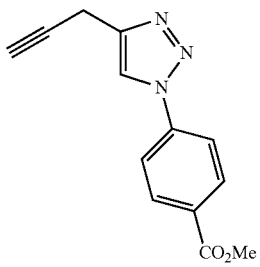

methyl 4-(4-(prop-2-ynyl)-1H-1,2,3-triazol-1-yl)benzoate

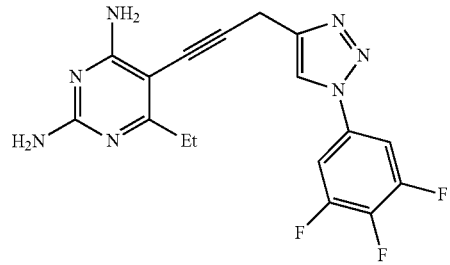

6-ethyl-5-(3-(1-(3,4,5-triflourophenyl)-1H-1,2,3-triazol-4-yl)prop-1-ynyl)pyrimidine-2,4-diamine
Molecular Weight: 373.34

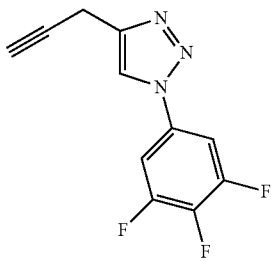

4-(prop-2-ynyl)-1-(3,4,5-triflourophenyl)-1H-1,2,3-triazole

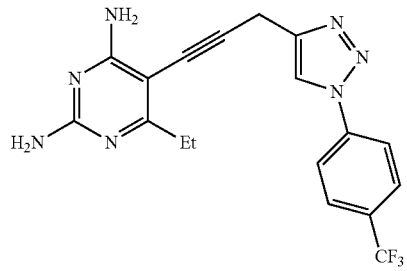

6-ethyl-5-(3-(1-(4-(triflouromethyl)phenyl)-1H-1,2,3-triazol-4-yl)prop-1-ynyl)pyrimidine-2,4-diamine
Molecular Weight: 387.36

-continued

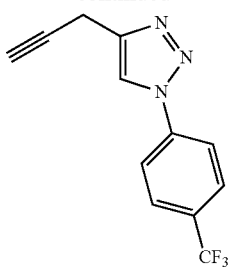

4-(prop-2-ynyl)-1-(4-(triflouromethyl)phenyl)-1H-1,2,3-triazole

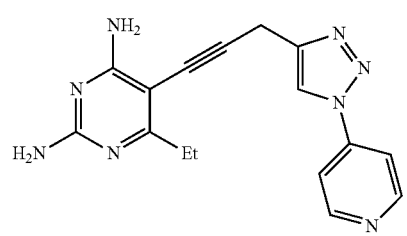

6-ethyl-5-(3-(1-(pyridin-4-yl)-1H-1,2,3-triazol-4-yl)prop-1-ynyl)pyrimidine-2,4-diamine
Molecular Weight: 320.35

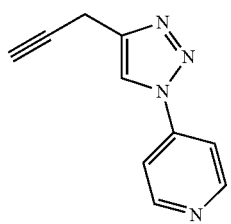

4-(4-(prop-2-ynyl)-1H-1,2,3-triazole-1yl)pyridine

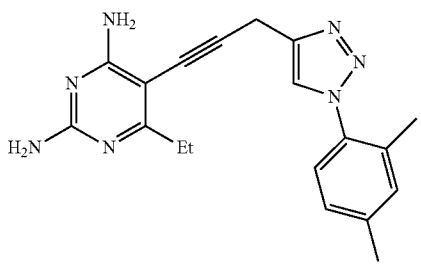

5-(3-(1-(2,4-dimethylphenyl)-1H-1,2,3-triazol-4-yl)prop-1-ynyl)-6-ethylpyrimidine-2,4-diamine
Molecular Weight: 347.42

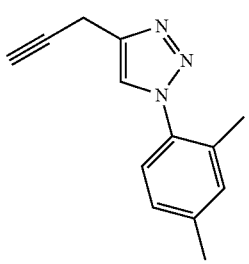

1-(2,4-dimethylphenyl)-4-(prop-2-ynyl)-1H-1,2,3-triazole

-continued

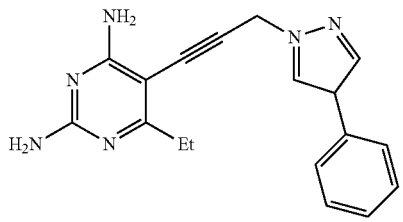

6-ethyl-5-(3-(4-phenyl-1H-pyrazol-1-yl)prop-1-ynyl)pyrimidine-2,4-diamine
Molecular Weight: 318.38

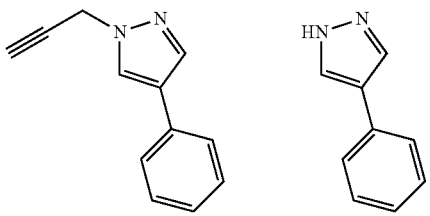

4-phenyl-1-(prop-2-ynyl)-1H-pyrazole    4-phenyl-1H-pyrazole

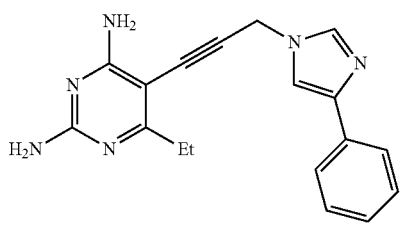

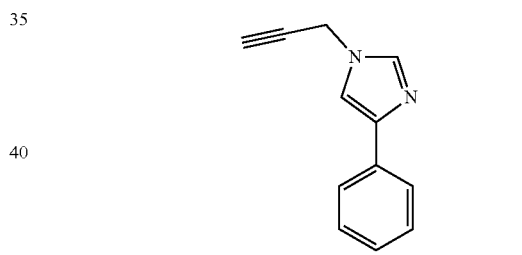

4-phenyl-1-(prop-2-ynyl)-1H-imidazole

Example 16

Additional compounds are prepared via the following schemes:

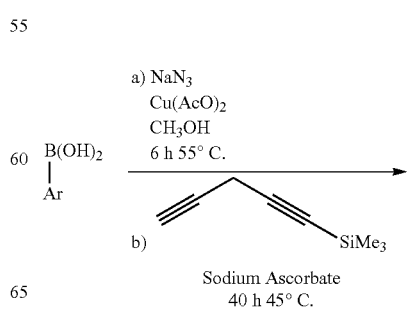

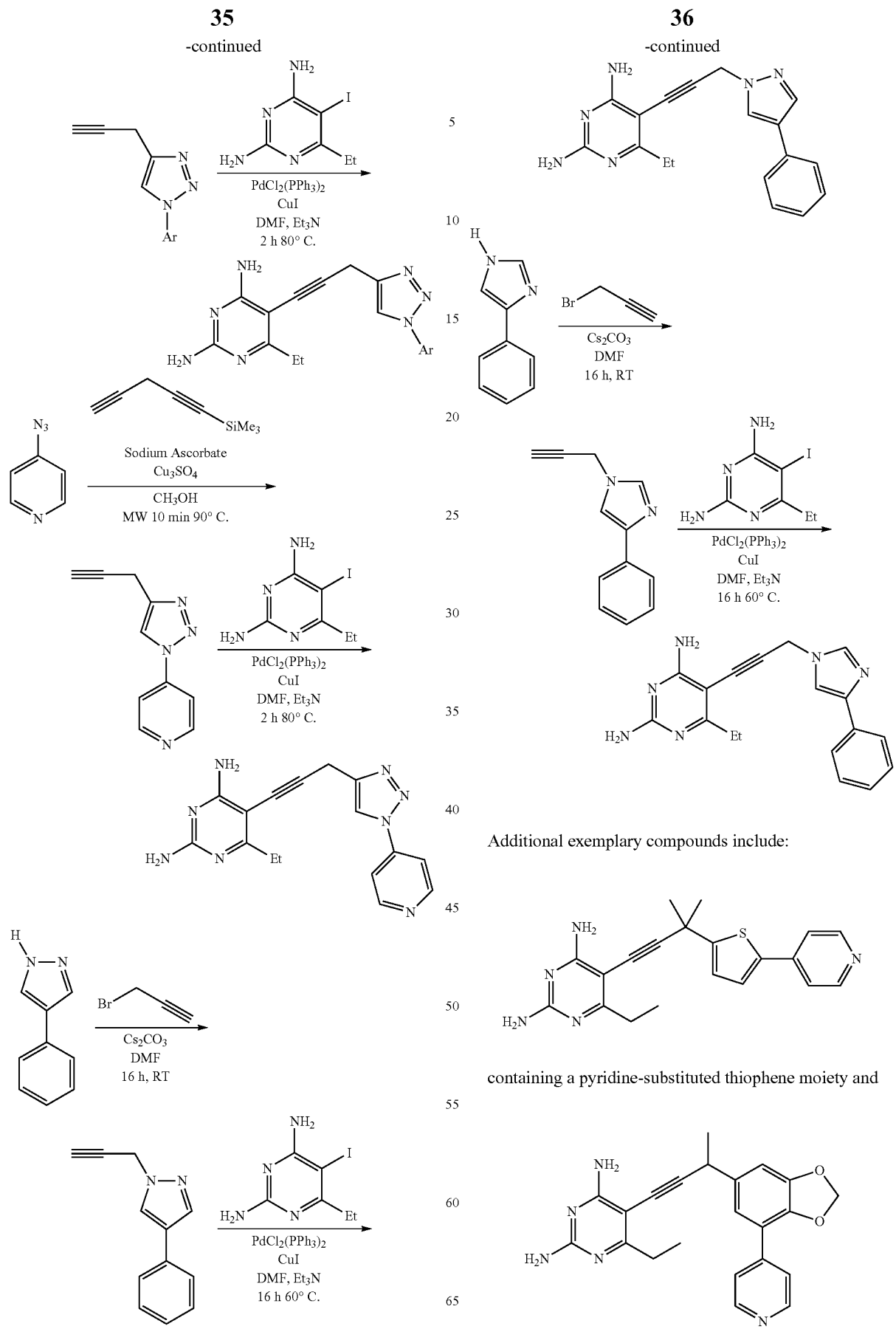
Additional exemplary compounds include:
containing a pyridine-substituted thiophene moiety and

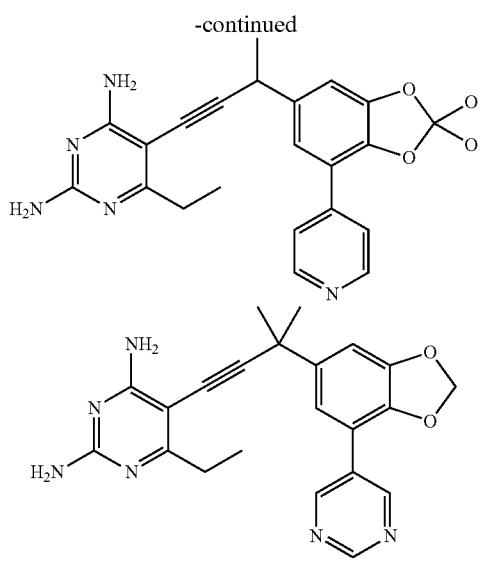

containing a pyridine-substituted benzodioxole or an amine pyrimidine-substituted benzodioxole.

The specific embodiments and examples of the invention as described herein are not limiting of the compounds, compositions and methods define by the claims. Additional embodiments within the scope of the claims will be apparent to those skilled in the art.

What is claimed is:

1. A compound of Formula I:

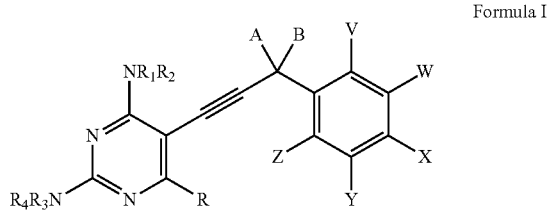

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, alkoxyalkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkylcarbonyl, haloalkylcarbonyl, and cyanoalkylcarbonyl;

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl;

wherein is an alkoxy group;

wherein at least one of W, X, Y, and Z is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

2. The compound of claim 1, wherein V is a methoxy group.

3. The compound of claim 2, wherein X is a phenyl group having at least one substituent selected from the group consisting of hydroxyl, cyano, carbamate (—OC(O)NH$_2$), methoxycarbonyl, methylamine and dimethylamine.

4. The compound of claim 1, wherein X is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine.

5. The compound of claim 1, wherein R is hydrogen or $C_{1-5}$alkyl, $R_1$, $R_2$, $R_3$, and $R_4$ are each independently selected from the group consisting of hydrogen, $C_{1-5}$alkyl, cycloalkyl, and alkoxyalkyl, and A and B are each independently hydrogen or $C_{1-5}$alkyl.

6. A compound of Formula IA:

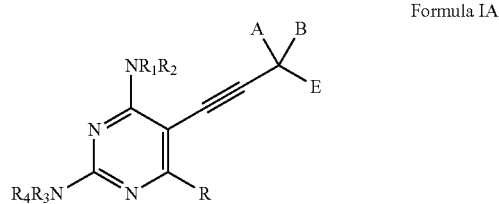

Formula IA wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, alkoxyalkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkylcarbonyl, haloalkylcarbonyl, and cyanoalkylcarbonyl;

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl; and wherein E is a heterocyclic substituent E1 selected from the group consisting of piperidine, perhydropyrimidine, morpholine, pyridine, pyrimidine, indole, isoindole, quinoline, isoquinoline, oxazole, thiazole, imidazole, furan, thiophene, pyrrole, pyrazole, triazole, tetrazole, isoxazole, oxadiazole, thiadiazole, isothiazole, pyridazine, pyrazine, benzofuran, benzothiophene, benzodioxole, indazole, piperazine, pyrrolidine, dioxolane, tetrahydrofuran, and tetrahydropyran, and wherein the heterocyclic substituent E1 itself is substituted with a heterocyclic or aryl substituent E2, which, in turn, may optionally be substituted one or more times with $C_1$ to $C_5$ alkyl, halogen, hydroxy, lower haloalkyl, lower alkoxy, lower haloalkoxy, or lower alkoxyalkyl, and the heterocyclic substituent E1 is optionally substituted one or more times with $C_1$ to $C_5$ alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, or dialkylsilyloxy;

wherein each "lower" used in conjunction with any of the above groups is individually $C_1$ to $C_6$, or a pharmaceutically acceptable salt thereof.

7. The compound of claim 6, wherein E1 is optionally substituted one or more times with $C_1$ to $C_5$ alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, or dialkylsilyloxy, and wherein E2 is attached to E1 in a meta or para arrangement.

8. The compound of claim 7, wherein E1 is selected from the group consisting of pyridine, pyrimidine, pyrazole, or triazole, optionally substituted one or more times with $C_1$ to $C_5$ alkyl, halogen, hydroxy, lower haloalkyl, lower alkoxy, lower haloalkoxy, or lower alkoxyalkyl, and E2 is phenyl or phenyl with one to three substituents individually selected from the group consisting of $C_1$ to $C_5$ alkyl, halogen, lower haloalkyl, lower alkoxy, lower haloalkoxy, lower alkoxyalkyl, and lower alkoxycarbonyl.

9. The compound of claim 6, wherein R is hydrogen or $C_{1-5}$alkyl, $R_1$, $R_2$, $R_3$, and $R_4$ are each independently selected from the group consisting of hydrogen, $C_{1-5}$alkyl, cycloalkyl, and alkoxyalkyl, and A and B are each independently hydrogen or $C_{1-5}$alkyl.

10. A pharmaceutical composition, comprising a compound of claim 1 in combination with one or more pharmaceutically acceptable diluents, excipients or carriers.

11. A pharmaceutical composition, comprising a compound of claim 6 in combination with one or more pharmaceutically acceptable diluents, excipients or carriers.

12. A method of treating an individual that has a fungal infection caused by *Candida* species, comprising administering a pharmaceutically effective amount of a compound of Formula I to the individual:

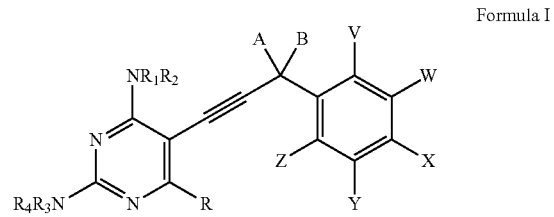

Formula I wherein R is selected from the group consisting of H, $C_{1-5}$alkyl, $C_{1-3}$alkoxy, and hydroxy;

wherein $R_1$, $R_2$, $R_3$ and $R_4$ are each independently selected from the group consisting of hydrogen, $C_{1-5}$ alkyl, and cycloalkyl;

wherein A and B are each independently selected from the group consisting of hydrogen, $C_{1-5}$alkyl, hydroxy, and lower alkoxy;

wherein V is an alkoxy group;

wherein at least one of W, X, Y, and Z is a phenyl group having at least one substituent selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of W, X, Y, and Z are each independently selected from the group consisting of hydrogen, $C_{1-5}$alkyl, halogen, hydroxy, lower haloalkyl, and phenyl, wherein the phenyl substituent may be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

13. The method of claim 12, wherein the fungal infection is caused by *C. albicans* or *C. glabrata*.

14. A method of treating an individual that has a fungal infection caused by *Candida* species, comprising administering a pharmaceutically effective amount of a compound of Formula IA to the individual:

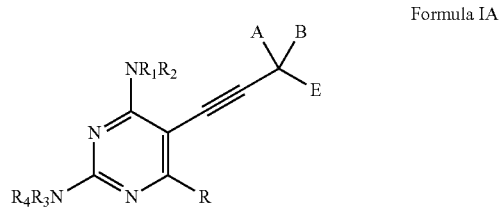

Formula IA wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, $C_{1-5}$alkyl, and cycloalkyl;

wherein A and B are each independently selected from the group consisting of hydrogen, $C_{1-5}$alkyl, hydroxy, and lower alkoxy; and wherein E is a heterocyclic substituent E1 selected from the group consisting of pyridine, pyrimidine, pyrazole, and triazole, optionally substituted one or more times with $C_1$ to $C_5$ alkyl, halogen, hydroxy, lower haloalkyl, lower alkoxy, lower haloalkoxy, or lower alkoxyalkyl, and optionally substituted with a phenyl or phenyl with one to three substituents individually selected from the group consisting of $C_1$ to $C_5$ alkyl, halogen, lower haloalkyl, lower alkoxy, lower haloalkoxy, lower alkoxyalkyl, and lower alkoxycarbonyl;

wherein each "lower" used in conjunction with any of the above groups is individually $C_1$ to $C_6$, or a pharmaceutically acceptable salt thereof.

15. The method of claim 14, wherein the fungal infection is caused by *C. albicans* or *C. glabrata*.

16. A compound of Formula I:

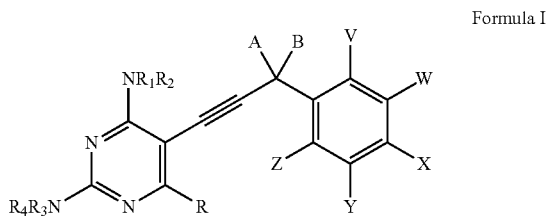

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, and $C_{1-5}$alkyl, cycloalkyl, alkoxyalkyl, alkoxyalkoxyalkyl, arylalkyl, alkylcarbonyl, cycloalkylcarbonyl, alkoxycarbonyl, alkoxyalkylcarbonyl, alkoxyalkoxyalkylcarbonyl, arylcarbonyl, pyridinylcarbonyl, aryloxyalkylcarbonyl, haloalkylcarbonyl, and cyanoalkylcarbonyl;

wherein A and B are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally substituted with halogen, lower haloalkyl, lower alkyl, lower alkoxy, or lower alkylsulfonyl;

wherein at least one of V, W, X, Y, and Z is an alkoxy group;

wherein at least one of V, W, X, Y, and Z is a phenyl group having at least one substituent in the para position and selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of V, W, X, Y, and Z are each independently selected from the group consisting of hydrogen, $C_{1-5}$alkyl, halogen, hydroxy, lower haloalkyl, lower alkoxy, lower haloalkoxy, lower alkoxyalkyl, carboxy, lower alkoxycarbonyl, cyano, nitro, aminocarbonyl, lower alkylsulfinyl, lower alkylcarbonylamino, lower alkylsulfonylamino, lower alkylthio, lower alkylsulfonyl, formyl, lower alkoxycarbonyl, dialkylsilyloxy, phenyl, phenoxy, arylalkoxy, and aryloxyalkoxy, wherein the phenyl, phenoxy, arylalkoxy, and aryloxyalkoxy substituents may themselves be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

17. The compound of claim 16, wherein at least one of V, W, X, Y, and Z is a methoxy group.

18. The compound of claim 16, wherein V is an alkoxy group.

19. The compound of claim 16, wherein V is a methoxy group.

20. The compound of claim 16, wherein X is a phenyl group having at least one substituent in the para position and selected from the group consisting of hydroxyl, cyano, carbamate (—OC(O)NH$_2$), methoxycarbonyl, methylamine and dimethylamine.

21. The compound of claim 16, wherein R is hydrogen or $C_{1-5}$alkyl, $R_1$, $R_2$, $R_3$, and $R_4$ are each independently selected from the group consisting of hydrogen, $C_{1-5}$alkyl, cycloalkyl, and alkoxyalkyl, and A and B are each independently hydrogen or $C_{1-5}$alkyl.

22. A pharmaceutical composition, comprising a compound of claim 16 in combination with one or more pharmaceutically acceptable diluents, excipients or carriers.

23. A method of treating an individual that has a fungal infection caused by *Candida* species, comprising administering a pharmaceutically effective amount of a compound of Formula I to the individual:

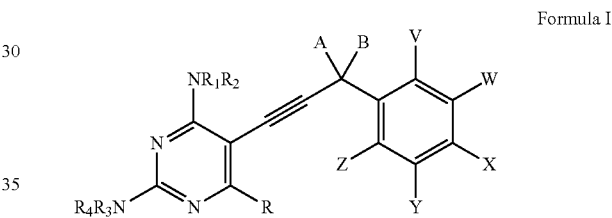

Formula I wherein R is selected from the group consisting of H, $C_{1-5}$alkyl, $C_{1-3}$alkoxy, and hydroxy;

wherein $R_1$, $R_2$, $R_3$, and $R_4$ are each independently selected from the group consisting of hydrogen, $C_{1-5}$alkyl, and cycloalkyl;

wherein A and B are each independently selected from the group consisting of hydrogen, $C_{1-5}$alkyl, hydroxy, and lower alkoxy;

wherein at least one of V, W, X, Y, and Z is an alkoxy group;

wherein at least one of V, W, X, Y, and Z is a phenyl group having at least one substituent in the para position and selected from the group consisting of hydroxyl, cyano, carbamate (—OC(O)NH$_2$), N-lower alkyl carbamate, N,N-di-lower alkyl carbamate, alkoxycarbonyl, lower alkyl amine and di-lower alkyl amine; and wherein the remainder of V, W, X, Y, and Z are each independently selected from the group consisting of hydrogen, $C_{1-5}$alkyl, halogen, hydroxy, lower haloalkyl, and phenyl, wherein the phenyl substituent may be optionally independently substituted one or more times with halogen, lower haloalkyl, lower alkyl, lower alkoxy, or lower alkylsulfonyl;

wherein each "lower" used in conjunction with any of the above groups is individually $C_1$ to $C_6$, or a pharmaceutically acceptable salt thereof.

24. The method of claim 23, wherein the fungal infection is caused by *C. albicans* or *C. glabrata*.

* * * * *